(12) United States Patent
Kostem

(10) Patent No.: US 11,423,306 B2
(45) Date of Patent: Aug. 23, 2022

(54) SYSTEMS AND DEVICES FOR CHARACTERIZATION AND PERFORMANCE ANALYSIS OF PIXEL-BASED SEQUENCING

(71) Applicant: Illumina, Inc., San Diego, CA (US)

(72) Inventor: Emrah Kostem, Menlo Park, CA (US)

(73) Assignee: Illumina, Inc., San Diego, CA (US)

( * ) Notice: Subject to any disclaimer, the term of this patent is extended or adjusted under 35 U.S.C. 154(b) by 40 days.

(21) Appl. No.: 16/874,599

(22) Filed: May 14, 2020

(65) Prior Publication Data

US 2020/0364496 A1 Nov. 19, 2020

Related U.S. Application Data

(60) Provisional application No. 62/849,091, filed on May 16, 2019, provisional application No. 62/849,132, (Continued)

(51) Int. Cl.
| | | |
|---|---|---|
| *G06K 9/62* | (2006.01) | |
| *G06N 3/08* | (2006.01) | |
| *G06N 3/04* | (2006.01) | |

(52) U.S. Cl.
CPC ............ *G06N 3/08* (2013.01); *G06K 9/6202* (2013.01); *G06K 9/6212* (2013.01); (Continued)

(58) Field of Classification Search
CPC ............ C12Q 1/6869; G01N 21/6428; G01N 21/6454; G06K 9/6202; G06K 9/6212; (Continued)

(56) References Cited

U.S. PATENT DOCUMENTS 10,168,438 B2 * 1/2019 Dennis ................... G01T 1/366
10,527,549 B2 * 1/2020 Rebetez ............. G01N 21/6452
(Continued)

FOREIGN PATENT DOCUMENTS

EP 3130681 A1 2/2017

OTHER PUBLICATIONS

Cacho et al. "A Comparison of Base-calling Algorithms for Illumina Sequencing Technology", Briefings in Bioinformatics, Oxford University Press, Oxford GB vol. 17, No. 5, Oct. 5, 2015 (Year: 2015).*
(Continued)

*Primary Examiner* — Ian L Lemieux
(74) *Attorney, Agent, or Firm* — Haynes Beffel & Wolfeld LLP; Ernest J. Beffel, Jr.; Sikander M. Kahn

(57) ABSTRACT

In one embodiment, a method of determining tag signals from measured intensities, the measured intensities collected by light sensors in a sensor array directed to a sample surface, the sample surface including pixel areas and holding a plurality of clusters during a sequence of sampling events, each light sensor directed to and measuring intensity from one of the pixel areas during each sampling period includes adjustments for background intensity and crosstalk and taking into account signal decay and phasing/pre-phasing. Coefficients for the adjustments can be determined by gradient descent, using as ground truth base calling by the system being characterized or by using reliable base calling of well-characterized sample run through the system being characterized.

20 Claims, 20 Drawing Sheets
(12 of 20 Drawing Sheet(s) Filed in Color)

Related U.S. Application Data filed on May 16, 2019, provisional application No. 62/849,133, filed on May 16, 2019.

(52) U.S. Cl.
CPC .............. *G06K 9/6214* (2013.01); *G06N 3/04* (2013.01); *G06N 3/0481* (2013.01)

(58) Field of Classification Search
CPC ...... G06K 9/6214; G06N 3/04; G06N 3/0454; G06N 3/0481; G06N 3/08; G06N 3/084; G16B 30/00; G16B 40/10
See application file for complete search history.

(56) References Cited

U.S. PATENT DOCUMENTS

| | | | | |
|---|---|---|---|---|
| 10,740,883 | B2* | 8/2020 | Zerfass | G06T 5/008 |
| 2003/0062485 | A1* | 4/2003 | Fernandez | G01N 33/582 |
| | | | | 250/458.1 |
| 2006/0040297 | A1* | 2/2006 | Leamon | G01N 21/6428 |
| | | | | 435/6.18 |
| 2012/0015825 | A1* | 1/2012 | Zhong | G01N 21/6428 |
| | | | | 506/6 |
| 2014/0152801 | A1* | 6/2014 | Fine | G02B 21/0008 |
| | | | | 348/79 |
| 2015/0169824 | A1* | 6/2015 | Kermani | G16B 30/10 |
| | | | | 702/19 |
| 2017/0044601 | A1* | 2/2017 | Crnogorac | C12Q 1/6874 |

OTHER PUBLICATIONS

Wang et al. "An adaptive decorrelation method removes Illumina DNA base-calling errors caused by crosstalk between adjacent clusters", Scientific Reports, vol. 7, No. 1, Feb. 20, 2017 (Year: 2017).*

PCT/US2020/033280 International Search Report and Written Opinion, dated Jul. 22, 2020, 18 pages.

PCT/US2020/033280 Article 34 Amendment, dated Apr. 19, 2021, 24 pages.

Wang et al., An adaptive decorrelation method removes Illumina DNA base-calling errors caused by crosstalk between adjacent clusters—with Supplemental Materials, Scientific Reports, published Feb. 20, 2017, 17 pages.

PCT/US2020/033280—International Preliminary Reporton Patentability, dated Jul. 23, 2021, 11 pages.

Pfeiffer et al., Systematic evaluation of error rates and causes in short samples in next-generation sequencing, Scientific Reports, published Jul. 19, 2018, 14 pages.

EP 20733084.6—Rules 161(2) and 162 Communication, dated Jan. 3, 2022, 3 pages.

Hacteria Wiki, HiSeq2000—Next Level Hacking—Hackteria Wiki, retrieved on Apr. 12, 2021, retrieved from the internet [URL: https://www.hackteria.org/wiki/HiSeq2000_-_Next_Level_Hacking ], 42 pages.

\* cited by examiner

Side View

Dual Well

Top View

Dual Well

Heat Map Analysis of Contributions to Measured Intent

Background Illum.

Background Sensors

Cross talk

Signal Decay

Pre-phasing (ahead)

Phasing (behind)

| Old results (that assumed single background level) 1610 | | | | | |
|---|---|---|---|---|---|
| 1.1-700nm | | top | left | bottom | right |
| 1101 | AT | 24.341909 | 19.829670 | 19.758838 | 15.628538 |
| | CT | 22.020275 | 17.317464 | 15.913662 | 15.561291 |
| 1102 | AT | 25.530696 | 19.007779 | 19.568504 | 19.609484 |
| | CT | 18.669829 | 16.893688 | 14.560277 | 19.392024 |
| 1103 | AT | 28.200664 | 18.122190 | 22.020823 | 18.537117 |
| | CT | 20.363927 | 17.324294 | 15.475405 | 19.852067 |

| New results (after accounting for mutiple background levels) 1660 | | | | | |
|---|---|---|---|---|---|
| 1.1-700nm | | top | left | bottom | right |
| 1101 | AT | 11.620936 | 12.536674 | 13.117650 | 9.950693 |
| | CT | 11.721442 | 10.781526 | 12.166851 | 8.833713 |
| 1102 | AT | 10.201675 | 12.127177 | 12.735259 | 11.259811 |
| | CT | 9.894503 | 10.465124 | 10.747423 | 10.657845 |
| 1103 | AT | 9.896417 | 11.748326 | 11.205233 | 11.560328 |
| | CT | 8.221915 | 11.101633 | 10.940892 | 8.717660 |

FIG. 16

SYSTEMS AND DEVICES FOR CHARACTERIZATION AND PERFORMANCE ANALYSIS OF PIXEL-BASED SEQUENCING

PRIORITY APPLICATIONS

This application claims priority to or the benefit of U.S. Provisional Patent Application No. 62/849,091, titled, "Systems and Devices for Characterization and Performance Analysis of Pixel-Based Sequencing," filed May 16, 2019; U.S. Provisional Patent Application No. 62/849,132, titled, "Base Calling using Convolutions," filed May 16, 2019; and U.S. Provisional Patent Application No. 62/849,133, titled, "Base Calling using Compact Convolutions," filed May 16, 2019. The provisional applications are hereby incorporated by reference for all purposes.

This application claims priority to U.S. Nonprovisional patent application Ser. No. 16/874,633, titled "Base Calling using Convolutions", filed contemporaneously. The Nonprovisional application is hereby incorporated by reference for all purposes.

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates to using deep neural networks such as deep convolutional neural networks for analyzing data.

INCORPORATIONS

The following are incorporated by reference for all purposes as if fully set forth herein:

U.S. Provisional Patent Application No. 62/821,602, titled "TRAINING DATA GENERATION FOR ARTIFICIAL INTELLIGENCE-BASED SEQUENCING,", filed on Mar. 21, 2019;

U.S. Provisional Patent Application No. 62/821,618, titled "TRAINING DATA GENERATION FOR ARTIFICIAL INTELLIGENCE-BASED SEQUENCING,", filed on Mar. 21, 2019;

U.S. Provisional Patent Application No. 62/821,681, titled "ARTIFICIAL INTELLIGENCE-BASED BASE CALLING,", filed on Mar. 21, 2019;

U.S. Provisional Patent Application No. 62/821,766, titled "ARTIFICIAL INTELLIGENCE-BASED SEQUENCING,", filed on Mar. 21, 2019;

U.S. Provisional Patent Application No. 62/821,724, titled "ARTIFICIAL INTELLIGENCE-BASED QUALITY SCORING,", filed on Mar. 21, 2019;

PCT Patent Application No. PCT/US2017/028883, titled "PHOTONIC STRUCTURE-BASED DEVICES AND COMPOSITIONS FOR USE IN LUMINESCENT IMAGING OF MULTIPLE SITES WITHIN A PIXEL, AND METHODS OF USING THE SAME," filed on Apr. 21, 2017, subsequently published as PCT Publication No. WO 2017/184997 A1, published on Oct. 26, 2017;

PCT Patent Application No. PCT/US2016/047253, titled "IN-LINE PRESSURE ACCUMULATOR AND FLOW-CONTROL SYSTEM FOR BIOLOGICAL OR CHEMICAL ASSAYS," filed on Aug. 17, 2016, subsequently published as PCT Publication No. WO 2017/034868 A1, published on Mar. 2, 2017;

PCT Patent Application No. PCT/US2017/038259, titled "SUPER-RESOLUTION MICROSCOPY," filed on Jun. 20, 2017, subsequently published as PCT Publication No. WO 2017/223041 A1, published on Dec. 28, 2017;

U.S. patent application Ser. No. 15/077,182 titled "METHODS, CARRIER ASSEMBLIES, AND SYSTEMS FOR IMAGING SAMPLES FOR BIOLOGICAL OR CHEMICAL ANALYSIS," filed on Mar. 22, 2016, subsequently published as US 2016/0281150 A1 on Sep. 29, 2016;

U.S. Pat. No. 9,193,998 B2, titled "SUPER RESOLUTION IMAGING," issued on Nov. 24, 2015;

U.S. Pat. No. 9,937,497 B2 titled "MICRODEVICES AND BIOSENSOR CARTRIDGES FOR BIOLOGICAL OR CHEMICAL ANALYSIS AND SYSTEMS AND METHODS FOR THE SAME," issued on Apr. 10, 2018;

US Publication No. US 2017/0189904 A1, titled "SYSTEMS AND METHODS FOR BIOCHEMICAL ANALYSIS INCLUDING A BASE INSTRUMENT AND ARE MOVABLE CARTRIDGE," published Jul. 6, 2017;

U.S. patent application Ser. No. 15/125,124, titled "DISPOSABLE, INTEGRATED MICROFLUIDIC CARTRIDGE AND METHODS OF MAKING AND USING SAME," filed Mar. 11, 2015, subsequently published as US 2017/0016060 A1 on Jan. 19, 2017;

European Patent Application No. 08781608.8, titled "METHOD AND APPARATUS USING ELECTRIC FIELD FOR IMPROVED BIOLOGICAL ASSAYS," EP Publication No. EP 2 173 467 B1, published May 4, 2016;

U.S. patent application Ser. No. 15/067,013, titled "INTEGRATED SEQUENCING APPARATUSES AND METHODS OF USE," filed Mar. 10, 2016, subsequently patented as U.S. Pat. No. 10,167,505 B2 and issued on Jan. 1, 2019; and U.S. patent application Ser. No. 13/882,088, titled "MICRODEVICES AND BIOSENSOR CARTRIDGES FOR BIOLOGICAL OR CHEMICAL ANALYSIS AND SYSTEMS AND METHODS FOR THE SAME," filed Apr. 26, 2013, subsequently patented as U.S. Pat. No. 9,096,899 B2 and issued on Aug. 4, 2015.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Various protocols in biological or chemical research involve performing a large number of controlled reactions on local support surfaces or within predefined reaction chambers (or wells). The desired reactions may then be observed or detected and subsequent analysis may help identify or reveal properties of chemicals involved in the reaction. For example, in some multiplex assays, an unknown analyte (e.g., clusters of clonally amplified nucleic acids) having an identifiable label (e.g., fluorescent label) may be exposed to thousands of known probes under controlled conditions. Each known probe may be deposited into a corresponding well of a microplate or flow cell. Observing any chemical reactions that occur between the known probes and the unknown analyte within the wells may help identify or reveal properties of the analyte. Other examples of such protocols include known DNA sequencing processes, such as sequencing-by-synthesis (SBS) or cyclic-array sequencing.

In some conventional fluorescent-detection protocols, an optical system is used to direct an excitation light onto fluorescently-labeled analytes and to also detect the fluorescent signals that may emit from the analytes. However, such optical systems can be relatively expensive and require a larger benchtop footprint. For example, the optical system may include an arrangement of lenses, filters, and light sources. In other proposed detection systems, the controlled reactions occur immediately over a solid-state imager (e.g., charged-coupled device (CCD) or a complementary metal-oxide-semiconductor (CMOS) sensor) that does not require a large optical assembly to detect the fluorescent emissions.

The proposed solid-state imaging systems will be so much different than prior optical systems that new methods and devices are required to characterize the solid-state near field imaging systems and analyze their performance. This is true both of systems that are limited to one cluster base call per sensor (or pixel) and to systems that read two or more clusters per pixel.

An opportunity arises to improve understanding of signal and noise in solid-state imaging systems, which will lead to improved designs and manufacturing processes, better quality control, and base calling technologies specifically adapted to the new systems, as they become available. The present disclosure addresses this need and provides other advantages as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The color drawings also may be available in PAIR via the Supplemental Content tab.

The present disclosure, in accordance with one or more embodiments, is described in detail with reference to the following figures. The figures are provided for purposes of illustration only and merely depict example embodiments. Furthermore, it should be noted that for clarity and ease of illustration, the elements in the figures have not necessarily been drawn to scale.

FIG. 16 includes tables that illustrate reduced estimates of crosstalk after accounting for multiple background levels intrinsic to individual sensors.

DETAILED DESCRIPTION

Figure 1:
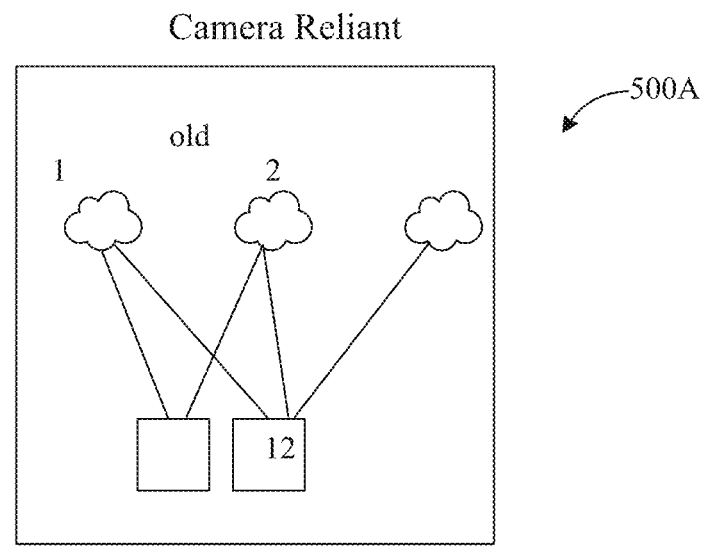
FIG. 1 shows a traditional design, in which multiple camera pixels capture a magnified image of a cluster on a substrate.

Embodiments described herein may be used in various biological or chemical processes and systems for academic or commercial analysis. More specifically, embodiments described herein may be used in various processes and systems where it is desired to detect an event, property, quality, or characteristic that is indicative of a desired reaction. For example, embodiments described herein include cartridges, biosensors, and their components as well as bioassay systems that operate with cartridges and biosensors. In particular embodiments, the cartridges and biosensors include a flow cell and one or more sensors, pixels, light detectors, or photodiodes that are coupled together in a substantially unitary structure.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be standalone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" or "including" an element or a plurality of elements having a particular property may include additional elements whether or not they have that property.

As used herein, a "desired reaction" includes a change in at least one of a chemical, electrical, physical, or optical property (or quality) of an analyte-of-interest. In particular embodiments, the desired reaction is a positive binding event (e.g., incorporation of a fluorescently labeled biomolecule with the analyte-of-interest). More generally, the desired reaction may be a chemical transformation, chemical change, or chemical interaction. The desired reaction may also be a change in electrical properties. For example, the desired reaction may be a change in ion concentration within a solution. Exemplary reactions include, but are not limited to, chemical reactions such as reduction, oxidation, addition, elimination, rearrangement, esterification, amidation, etherification, cyclization, or substitution; binding interactions in which a first chemical binds to a second chemical; dissociation reactions in which two or more chemicals detach from each other; fluorescence; luminescence; bioluminescence; chemiluminescence; and biological reactions, such as nucleic acid replication, nucleic acid amplification, nucleic acid hybridization, nucleic acid ligation, phosphorylation, enzymatic catalysis, receptor binding, or ligand binding. The desired reaction can also be an addition or elimination of a proton, for example, detectable as a change in pH of a surrounding solution or environment. An additional desired reaction can be detecting the flow of ions across a membrane (e.g., natural or synthetic bilayer membrane), for example as ions flow through a membrane the current is disrupted and the disruption can be detected.

In particular embodiments, the desired reaction includes the incorporation of a fluorescently-labeled molecule to an analyte. The analyte may be an oligonucleotide and the fluorescently-labeled molecule may be a nucleotide. The desired reaction may be detected when an excitation light is directed toward the oligonucleotide having the labeled nucleotide, and the fluorophore emits a detectable fluorescent signal. In alternative embodiments, the detected fluorescence is a result of chemiluminescence or bioluminescence. A desired reaction may also increase fluorescence (or Förster) resonance energy transfer (FRET), for example, by bringing a donor fluorophore in proximity to an acceptor fluorophore, decrease FRET by separating donor and acceptor fluorophores, increase fluorescence by separating a quencher from a fluorophore or decrease fluorescence by co-locating a quencher and fluorophore.

As used herein, a "reaction component" or "reactant" includes any substance that may be used to obtain a desired reaction. For example, reaction components include reagents, enzymes, samples, other biomolecules, and buffer solutions. The reaction components are typically delivered to a reaction site in a solution and/or immobilized at a reaction site. The reaction components may interact directly or indirectly with another substance, such as the analyte-of-interest.

As used herein, the term "reaction site" is a localized region where a desired reaction may occur. A reaction site may include support surfaces of a substrate where a substance may be immobilized thereon. For example, a reaction site may include a substantially planar surface in a channel of a flow cell that has a colony of nucleic acids thereon. Typically, but not always, the nucleic acids in the colony have the same sequence, being for example, clonal copies of a single stranded or double stranded template. However, in some embodiments a reaction site may contain only a single nucleic acid molecule, for example, in a single stranded or double stranded form. Furthermore, a plurality of reaction sites may be unevenly distributed along the support surface or arranged in a predetermined manner (e.g., side-by-side in a matrix, such as in microarrays). A reaction site can also include a reaction chamber (or well) that at least partially defines a spatial region or volume configured to compartmentalize the desired reaction.

This application uses the terms "reaction chamber" and "well" interchangeably. As used herein, the term "reaction chamber" or "well" includes a spatial region that is in fluid communication with a flow channel. The reaction chamber may be at least partially separated from the surrounding environment or other spatial regions. For example, a plurality of reaction chambers may be separated from each other by shared walls. As a more specific example, the reaction chamber may include a cavity defined by interior surfaces of a well and have an opening or aperture so that the cavity may be in fluid communication with a flow channel. Biosensors including such reaction chambers are described in greater detail in international application no. PCT/US2011/057111, filed on Oct. 20, 2011, which is incorporated herein by reference in its entirety.

In some embodiments, the reaction chambers are sized and shaped relative to solids (including semi-solids) so that the solids may be inserted, fully or partially, therein. For example, the reaction chamber may be sized and shaped to accommodate only one capture bead. The capture bead may have clonally amplified DNA or other substances thereon. Alternatively, the reaction chamber may be sized and shaped to receive an approximate number of beads or solid substrates. As another example, the reaction chambers may also be filled with a porous gel or substance that is configured to control diffusion or filter fluids that may flow into the reaction chamber.

In some embodiments, sensors (e.g., light detectors, photodiodes) are associated with corresponding pixel areas of a sample surface of a biosensor. As such, a pixel area is a geometrical construct that represents an area on the biosensor's sample surface for one sensor (or pixel). A sensor that is associated with a pixel area detects light emissions gathered from the associated pixel area when a desired reaction has occurred at a reaction site or a reaction chamber overlying the associated pixel area. In a flat surface embodiment, the pixel areas can overlap. In some cases, a plurality of sensors may be associated with a single reaction site or a single reaction chamber. In other cases, a single sensor may be associated with a group of reaction sites or a group of reaction chambers.

As used herein, a "biosensor" includes a structure having a plurality of reaction sites and/or reaction chambers (or wells). A biosensor may include a solid-state imaging device (e.g., CCD or CMOS imager) and, optionally, a flow cell mounted thereto. The flow cell may include at least one flow channel that is in fluid communication with the reaction sites and/or the reaction chambers. As one specific example, the biosensor is configured to fluidically and electrically couple to a bioassay system. The bioassay system may deliver reactants to the reaction sites and/or the reaction chambers according to a predetermined protocol (e.g., sequencing-by-synthesis) and perform a plurality of imaging events. For example, the bioassay system may direct solutions to flow along the reaction sites and/or the reaction chambers. At least one of the solutions may include four types of nucleotides having the same or different fluorescent labels. The nucleotides may bind to corresponding oligonucleotides located at the reaction sites and/or the reaction chambers. The bioassay system may then illuminate the reaction sites and/or the reaction chambers using an excitation light source (e.g., solid-state light sources, such as light-emitting diodes or LEDs). The excitation light may have a predetermined wavelength or wavelengths, including a range of wavelengths. The excited fluorescent labels provide emission signals that may be captured by the sensors.

In alternative embodiments, the biosensor may include electrodes or other types of sensors configured to detect other identifiable properties. For example, the sensors may be configured to detect a change in ion concentration. In another example, the sensors may be configured to detect the ion current flow across a membrane.

As used herein, a "cluster" is a colony of similar or identical molecules or nucleotide sequences or DNA strands. For example, a cluster can be an amplified oligonucleotide or any other group of a polynucleotide or polypeptide with a same or similar sequence. In other embodiments, a cluster can be any element or group of elements that occupy a physical area on a sample surface. In embodiments, clusters are immobilized to a reaction site and/or a reaction chamber during a base calling cycle.

As used herein, the term "immobilized," when used with respect to a biomolecule or biological or chemical substance, includes substantially attaching the biomolecule or biological or chemical substance at a molecular level to a surface. For example, a biomolecule or biological or chemical substance may be immobilized to a surface of the substrate material using adsorption techniques including non-covalent interactions (e.g., electrostatic forces, van der Waals, and dehydration of hydrophobic interfaces) and covalent binding techniques where functional groups or linkers facilitate attaching the biomolecules to the surface. Immobilizing biomolecules or biological or chemical substances to a surface of a substrate material may be based upon the properties of the substrate surface, the liquid medium carrying the biomolecule or biological or chemical substance, and the properties of the biomolecules or biological or chemical substances themselves. In some cases, a substrate surface may be functionalized (e.g., chemically or physically modified) to facilitate immobilizing the biomolecules (or biological or chemical substances) to the substrate surface. The substrate surface may be first modified to have functional groups bound to the surface. The functional groups may then bind to biomolecules or biological or chemical substances to immobilize them thereon. A substance can be immobilized to a surface via a gel, for example, as described in US Patent Publ. No. US 2011/0059865 A1, which is incorporated herein by reference.

In some embodiments, nucleic acids can be attached to a surface and amplified using bridge amplification. Useful bridge amplification methods are described, for example, in U.S. Pat. No. 5,641,658; WO 2007/010251, U.S. Pat. No. 6,090,592; U.S. Patent Publ. No. 2002/0055100 A1; U.S. Pat. No. 7,115,400; U.S. Patent Publ. No. 2004/0096853 A1; U.S. Patent Publ. No. 2004/0002090 A1; U.S. Patent Publ. No. 2007/0128624 A1; and U.S. Patent Publ. No. 2008/0009420 A1, each of which is incorporated herein in its entirety. Another useful method for amplifying nucleic acids on a surface is rolling circle amplification (RCA), for example, using methods set forth in further detail below. In some embodiments, the nucleic acids can be attached to a surface and amplified using one or more primer pairs. For example, one of the primers can be in solution and the other primer can be immobilized on the surface (e.g., 5'-attached). By way of example, a nucleic acid molecule can hybridize to one of the primers on the surface followed by extension of the immobilized primer to produce a first copy of the nucleic acid. The primer in solution then hybridizes to the first copy of the nucleic acid which can be extended using the first copy of the nucleic acid as a template. Optionally, after the first copy of the nucleic acid is produced, the original nucleic acid molecule can hybridize to a second immobilized primer on the surface and can be extended at the same time or after the primer in solution is extended. In any embodiment, repeated rounds of extension (e.g., amplification) using the immobilized primer and primer in solution provide multiple copies of the nucleic acid.

In particular embodiments, the assay protocols executed by the systems and methods described herein include the use of natural nucleotides and also enzymes that are configured to interact with the natural nucleotides. Natural nucleotides include, for example, ribonucleotides (RNA) or deoxyribonucleotides (DNA). Natural nucleotides can be in the mono-, di-, or tri-phosphate form and can have a base selected from adenine (A), thymine (T), uracil (U), guanine (G) or cytosine (C). It will be understood however that non-natural nucleotides, modified nucleotides or analogs of the aforementioned nucleotides can be used. Some examples of useful non-natural nucleotides are set forth below in regard to reversible terminator-based sequencing by synthesis methods.

In embodiments that include reaction chambers, items or solid substances (including semi-solid substances) may be disposed within the reaction chambers. When disposed, the item or solid may be physically held or immobilized within the reaction chamber through an interference fit, adhesion, or entrapment. Exemplary items or solids that may be disposed within the reaction chambers include polymer beads, pellets, agarose gel, powders, quantum dots, or other solids that may be compressed and/or held within the reaction chamber. In particular embodiments, a nucleic acid superstructure, such as a DNA ball, can be disposed in or at a reaction chamber, for example, by attachment to an interior surface of the reaction chamber or by residence in a liquid within the reaction chamber. A DNA ball or other nucleic acid superstructure can be preformed and then disposed in or at the reaction chamber. Alternatively, a DNA ball can be synthesized in situ at the reaction chamber. A DNA ball can be synthesized by rolling circle amplification to produce a concatamer of a particular nucleic acid sequence and the concatamer can be treated with conditions that form a relatively compact ball. DNA balls and methods for their synthesis are described, for example in, U.S. Patent Publication Nos. 2008/0242560 A1 or 2008/0234136 A1, each of which is incorporated herein in its entirety. A substance that is held or disposed in a reaction chamber can be in a solid, liquid, or gaseous state.

As used herein, "base calling" identifies a nucleotide base in a nucleic acid sequence. Base calling refers to the process of determining a base call (A, C, G, T) for every cluster at a specific cycle. As an example, base calling can be performed utilizing four-channel, two-channel or one-channel methods and systems described in the incorporated materials of U.S. Patent Application Publication No. 2013/0079232. In particular embodiments, a base calling cycle is referred to as a "sampling event." In one dye and two-channel sequencing protocol, a sampling event comprises two illumination stages in time sequence, such that a pixel signal is generated at each stage. The first illumination stage induces illumination from a given cluster indicating nucleotide bases A and T in a AT pixel signal, and the second illumination stage induces illumination from a given cluster indicating nucleotide bases C and T in a CT pixel signal.

Introduction

A new approach to flow cell design involves nano wells in which one or two clusters are amplified. FIG. 1 shows a traditional design, in which multiple camera pixels capture a magnified image of a cluster on a substrate. In one design, a nano well is built on top of a CMOS sensor substrate. See application Ser. No. 16/241,905. In another design, a sensor is positioned directly over the nano well. In both designs, a sampling device includes a sample surface having an array of pixel areas and a solid-state array of sensors. Each sensor generates pixel signals in base calling cycles. The pixel signals represent light gathered from a corresponding pixel area of the sample surface. In some implementations, a sensor collects light from two wells. In other implementations, off axis illumination can distinguish signals from two clusters growing in one well. This is much different from prior camera-reliant, far field imaging approaches.

Fluidic channels carry reagents over and through the nano wells during sequencing. In each cycle, light energy, such as laser illumination, stimulates fluorescent tags attached to sequences to glow, signaling the current nucleotide in the sequence. Light from the tags is collected by the sensors. Using alternative chemistries, one, two or four illuminations produce an equal number of intensity maps. These are near field intensity maps, as distinct from photographic images, more like sensing a pen stroke than taking a picture.

An opportunity arises to characterize response of the tags to stimulation, to analyze performance of the new designs. Results of characterization guide cell design, manufacturing and operation. Results of characterization also can be applied to improve base calling.

Flow cells with one sensor per well are a relatively new design for parallel sequencing of millions of amplified clusters. Rapid development and future advances in technology are inevitable, as sequencing has advanced rapidly, with computational improvements and cost reductions at rates following Moore's law. Each new design needs to be characterized and analyzed for performance.

Consider part of a massively parallel design including a patch of nine CMOS sensors overlaid by filters and nano wells. The nano wells are sized to accommodate amplification and growth of one or two clusters (FIGS. 2, 3A-B) or alternatively to hold a micro bead on which a sequence is synthesized. Suppose that in each cycle of synthesis, the nano wells are illuminated by a red laser and then a green laser. Fluorescence of tags in clusters in the nano wells are collected by the CMOS sensors in red and green channels. Suppose the synthesis proceeds and calls bases for 150 cycles.

Development of the technology disclosed began with physical analysis of contributions to sensed intensity. Analysis revealed that, as sequencing proceeds, accurate base calling becomes increasingly difficult, because signal strength decreases and noise increases (FIG. 4), resulting in a substantially decreased signal-to-noise ratio. Physically, it was observed that later synthesis steps attach tags in a different position relative to the sensor than earlier synthesis steps. When the sensor is below a sequence that is being synthesized, signal decay results from attaching tags to strands (206A) further away from the sensor (206) in later sequencing steps than in earlier steps. We refer to this as signal decay. In some designs, where the sensor is above the substrate that holds cluster, signal could increase, instead of decay, as sequencing proceeds.

In the flow cell design investigated, while the signal decays, noise grows. Physically, phasing and pre-phasing (505) increase noise as sequencing proceeds. Phasing refers to steps in sequencing in which tags fail to advance along the sequence. Pre-phasing refers to sequencing steps in which tags jump two positions forward instead of one, during a sequencing cycle. Phasing and pre-phasing are both relatively infrequent (FIG. 10, phasing kernel), on the order of once in 500 to 1000 cycles. Phasing is slightly more frequent than pre-phasing. Phasing and pre-phasing impact individual strands in a cluster that is producing intensity data, so the intensity noise distribution from a cluster accumulates in a binomial, trinomial, quadranomial, etc. expansion (513) as sequencing proceeds. Graphically, this is depicted as a widening distribution cone (517) of sequencing progress among strands in a cluster as sequencing proceeds.

Figure 13A:
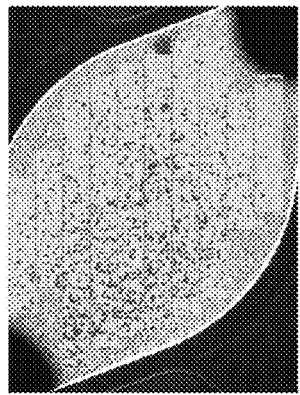
FIGS. 13A-F are a series of heat maps created by applying false color to a photograph of a flow cell, based on analysis of contributions of various factors to measured intensities in an intensity map for one channel.

Two additional sources contribute to sensor readouts of intensity. See, FIG. 13. They are cross talk and background. In a patch of nine sensors, the middle sensor receives crosstalk noise from at least four adjoining nano wells to the north, south, east and west (top, bottom, left and right) of center. Square or nearly square pixels in the checkerboard pattern receive more crosstalk from the primary points of the compass than from the diagonals. Investigation revealed that crosstalk is not symmetrical. FIG. 13C. Contributions to asymmetry appear to relate to the manufacturing of flow cells and positioning of the illumination source. Cross talk is a factor of intensity measured in the adjoining cells, which varies between cycles, because cross talk is the portion of the signal from the adjoining cells that leaks into the middle cell.

Figure 14A:
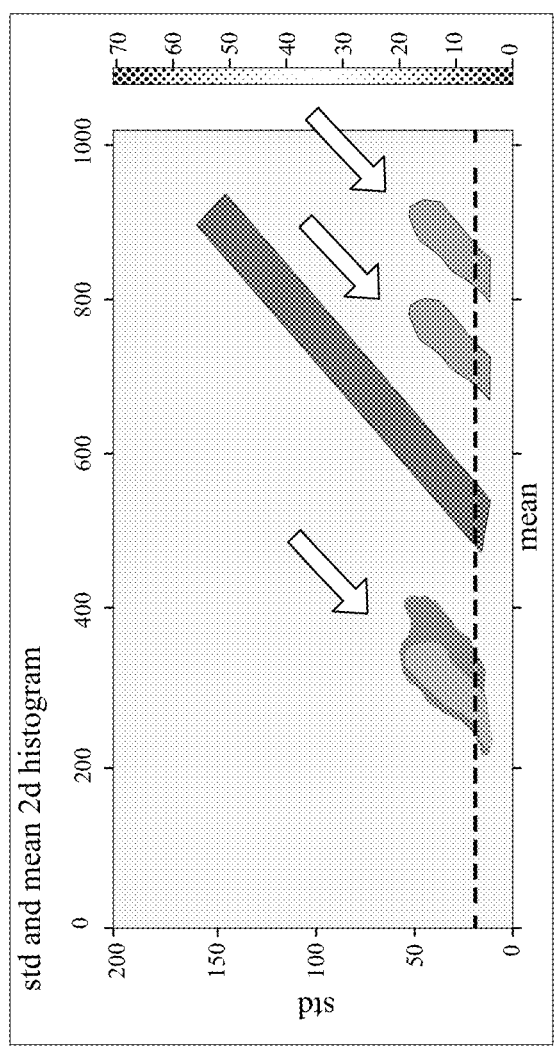
FIGS. 14A-B reflect sensor-specific variation in background readings that is not randomly distributed.
Figure 14B:
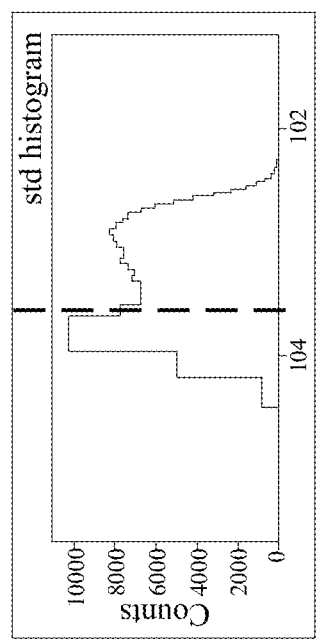
Figure 15:
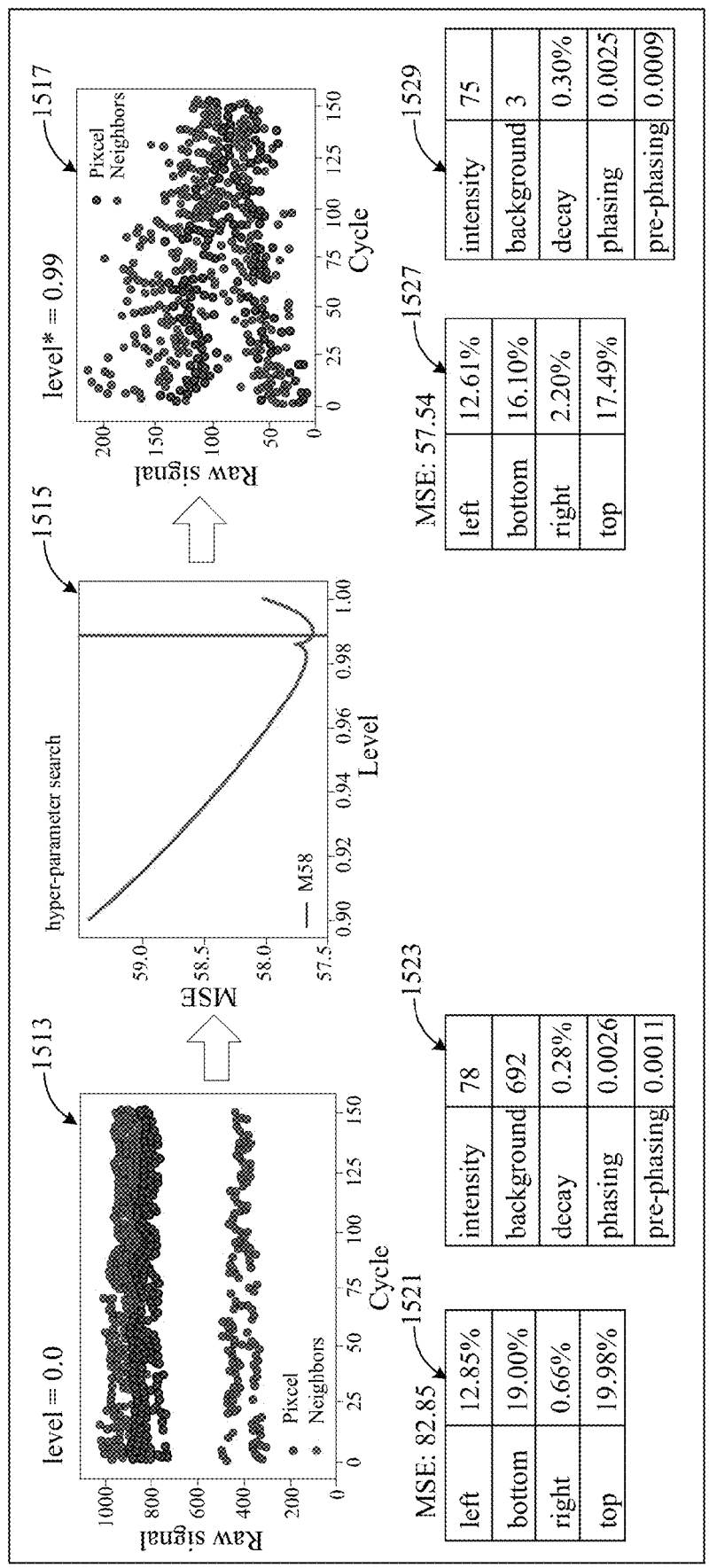
FIG. 15 presents a background level hyper-parameter approach to setting a particular pixel's background level taking into account background levels of its neighbors.
Figure 17:
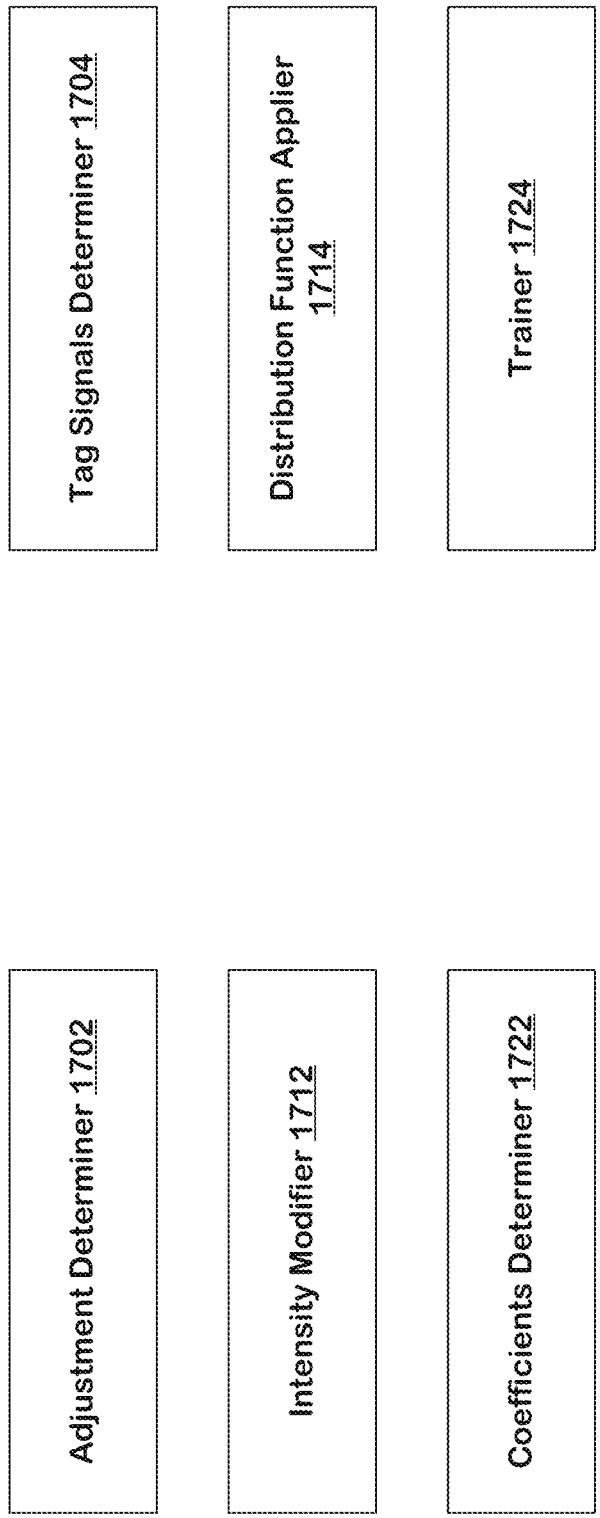
FIG. 17 shows various modules that implement the technology disclosed.

Background intensity of a particular cell is relatively steady between cycles, but varies across the sensors. FIG. 14A-B. Positioning of the illumination source, which can vary by illumination color, creates a spatial pattern of background variation over a field of the sensors. FIG. 13A. Surprisingly, manufacturing differences among the sensors were observed to produce different background intensity readouts, even between adjoining sensors. FIG. 15. In a first approximation, idiosyncratic variation among sensors can be ignored. In a refinement, the idiosyncratic variation in background intensity among sensors can be taken into account, with the surprising improvement in estimation of crosstalk effects. FIG. 16.

In one model, background intensity is a constant parameter to be fit, either overall or per pixel. In the refinement, different background intensities are taken into account when estimating crosstalk. FIGS. 14A-B, 15. Using background intensity applicable to sensors in a patch of nine, for instance, an improvement in mean squared error is achieved and cross talk estimations become more realistic, decreasing by half in some directions and increasing above negligible in others. FIG. 16.

An equation that approximates relationships among contributors to measured intensity is:

$$\mathcal{Y} = d_\circ \, s\mathcal{W}_{u'} \mathcal{H}_{c+} \mathscr{b}, \text{ wherein}$$

$\mathcal{Y}$ is a vector of measured intensities for a measurement channel over n cycles (e.g., 150), such as from a middle sensor in a patch of 9, c is a vector of measured intensities over n cycles from sensors north, south, east and west of the middle sensor, u is a Boolean vector indicating an active signal, over n cycles, which indicates whether a tag that is in correct time (not phasing or pre-phasing) emits a signal for the particular intensity measurement channel, which derives from base calling, d is an estimated decay (or increase) vector for a decreasing proportion of tag florescence that a sensor measures over the n cycles, which reduces the signal, $\mathcal{W}$ is an estimated matrix of signal distributions, over phasing (behind), in correct time, and pre-phasing (ahead) tag fluorescence, over the n cycles, which is an increasing part of the noise that grows over cycles, $\mathcal{H}$ is an estimated matrix of cross-talk contributions to measured intensity $\mathcal{Y}$ of the middle sensor that spills over from measured intensities e of the sensors north, south, east and west of the middle sensor, which is a varying part of the noise that is a factor of measured adjoining intensities, $\mathcal{b}$ is an estimated background intensity contribution to measured intensity $\mathcal{Y}$, which is a steady part of the noise, which may be individualized to the middle pixel, spatially and/or idiosyncratically, and $\mathcal{S}$ is a derived signal emanating from one or two clusters in a nano well measured by the middle cell, the signal. Solving for $\mathcal{S}$:

$$\frac{y - \mathcal{H} c - \mathcal{b}}{d \circ \mathcal{W} u} = \mathcal{S}$$

Does this work? What are the rules for rearranging the dot product in a solution?

This equation is for illustration purposes because, as described above, estimation of cross-talk can depend on idiosyncratic variations in background measurements between adjoining sensors. The equation applies separately to each intensity measurement channel, though estimated parameter values may be similar. The same characterization approach could be applied to an overhead sensor, as opposed to a substrate sensor, with the decay vector liable to become an increase vector, as florescent tagging approaches the sensor.

Base Calling System

The technology disclosed for use with an advanced system (653, 673) is generally applicable to base calling systems such as depicted in FIG. 1 of U.S. Nonprovisional patent application Ser. No. 16/241,902, referenced above.

Biosensor

Figure 2:
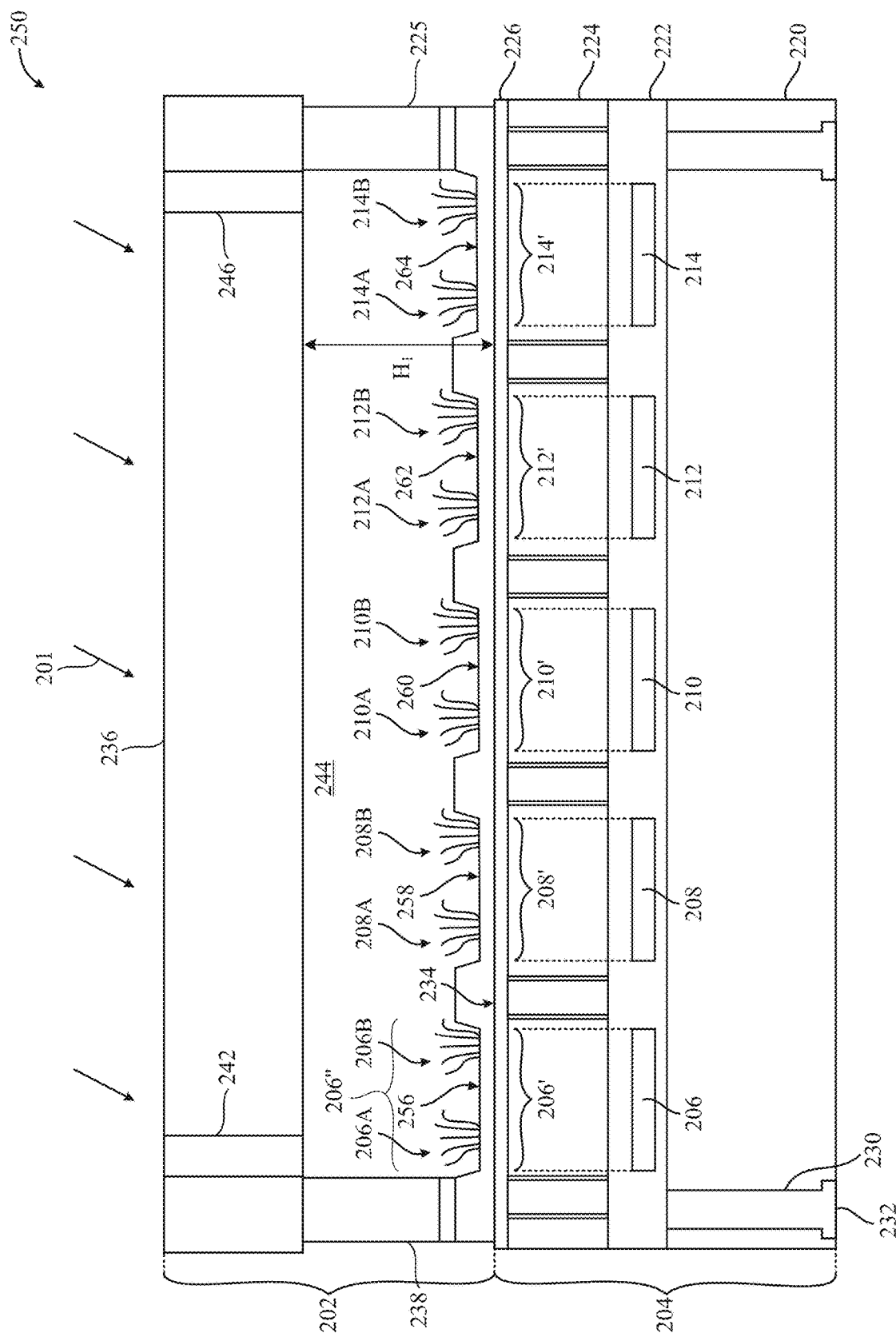
FIG. 2 illustrates a cross-section of a biosensor that can be used in various embodiments.

FIG. 2 illustrates a cross-section of a biosensor 200 that can be used in various embodiments. Biosensor 200 has pixel areas 206', 208', 210', 212', and 214' that can each hold more than one cluster during a base calling cycle (e.g., 2 clusters per pixel area). As shown, the biosensor 200 may include a flow cell 202 that is mounted onto a sampling device 204. In the illustrated embodiment, the flow cell 202 is affixed directly to the sampling device 204. However, in alternative embodiments, the flow cell 202 may be removably coupled to the sampling device 204. The sampling device 204 has a sample surface 234 that may be functionalized (e.g., chemically or physically modified in a suitable manner for conducting the desired reactions). For example, the sample surface 234 may be functionalized and may include a plurality of pixel areas 206', 208', 210', 212', and 214' that can each hold more than one cluster during a base calling cycle (e.g., each having a corresponding cluster pair 206AB, 208AB, 210AB, 212AB, and 214AB immobilized thereto). Each pixel area is associated with a corresponding sensor (or pixel or photodiode) 206, 208, 210, 212, and 214, such that light received by the pixel area is captured by the corresponding sensor. A pixel area 206' can be also associated with a corresponding reaction site 206" on the sample surface 234 that holds a cluster pair, such that light emitted from the reaction site 206" is received by the pixel area 206' and captured by the corresponding sensor 206. As a result of this sensing structure, in the case in which two or more clusters are present in a pixel area of a particular sensor during a base calling cycle (e.g., each having a corresponding cluster pair), the pixel signal in that base calling cycle carries information based on all of the two or more clusters. As a result, signal processing as described herein is used to distinguish each cluster, where there are more clusters than pixel signals in a given sampling event of a particular base calling cycle.

In the illustrated embodiment, the flow cell 202 includes sidewalls 238, 240 and a flow cover 236 that is supported by the sidewalls 238, 240. The sidewalls 238, 240 are coupled to the sample surface 234 and extend between the flow cover 236 and the sidewalls 238, 240. In some embodiments, the sidewalls 238, 240 are formed from a curable adhesive layer that bonds the flow cover 236 to the sampling device 204.

The sidewalls 238, 240 are sized and shaped so that a flow channel 244 exists between the flow cover 236 and the sampling device 204. As shown, the flow channel 244 may include a height $H_1$ that is determined by the sidewalls 238, 240. The height $H_1$ may be between about 50-400 µm (micrometer) or, more particularly, about 80-200 µm. In the illustrated embodiment, the height $H_1$ is about 100 µm. The flow cover 236 may include a material that is transparent to excitation light 201 propagating from an exterior of the biosensor 200 into the flow channel 244. As shown in FIG. 2, the excitation light 201 approaches the flow cover 236 at a non-orthogonal angle. However, this is only for illustrative purposes as the excitation light 201 may approach the flow cover 236 from different angles.

Also shown, the flow cover 236 may include inlet and outlet ports 242, 246 that are configured to fluidically engage other ports (not shown). For example, the other ports may be from the cartridge or the workstation. The flow channel 244 is sized and shaped to direct a fluid along the sample surface 234. The height $H_1$ and other dimensions of the flow channel 244 may be configured to maintain a substantially even flow of a fluid along the sample surface 234. The dimensions of the flow channel 244 may also be configured to control bubble formation.

As shown in the example of FIG. 2, the sidewalls 238, 240 and the flow cover 236 are separate components that are coupled to each other. In alternative embodiments, the sidewalls 238, 240 and the flow cover 236 may be integrally formed such that the sidewalls 238, 240 and the flow cover 236 are formed from a continuous piece of material. By way of example, the flow cover 236 (or the flow cell 202) may comprise a transparent material, such as glass or plastic. The flow cover 236 may constitute a substantially rectangular block having a planar exterior surface and a planar inner surface that defines the flow channel 244. The block may be mounted onto the sidewalls 238, 240. Alternatively, the flow cell 202 may be etched to define the flow cover 236 and the sidewalls 238, 240. For example, a recess may be etched into the transparent material. When the etched material is mounted to the sampling device 204, the recess may become the flow channel 244.

The sampling device 204 may be similar to, for example, an integrated circuit comprising a plurality of stacked substrate layers 220-226. The substrate layers 220-226 may include a base substrate 220, a solid-state imager 222 (e.g., CMOS image sensor), a filter or light-management layer 224, and a passivation layer 226. It should be noted that the above is only illustrative and that other embodiments may include fewer or additional layers. Moreover, each of the substrate layers 220-226 may include a plurality of sub-layers. As will be described in greater detail below, the sampling device 204 may be manufactured using processes that are similar to those used in manufacturing integrated circuits, such as CMOS image sensors and CCDs. For example, the substrate layers 220-226 or portions thereof may be grown, deposited, etched, and the like to form the sampling device 204.

The passivation layer 226 is configured to shield the filter layer 224 from the fluidic environment of the flow channel 244. In some cases, the passivation layer 226 is also configured to provide a solid surface (i.e., the sample surface 234) that permits biomolecules or other analytes-of-interest to be immobilized thereon. For example, each of the reaction sites may include a cluster of biomolecules that are immobilized to the sample surface 234. Thus, the passivation layer 226 may be formed from a material that permits the reaction sites to be immobilized thereto. The passivation layer 226 may also comprise a material that is at least transparent to a desired fluorescent light. By way of example, the passivation layer 226 may include silicon nitride ($Si_3N_4$) and/or silica ($SiO_2$). However, other suitable material(s) may be used. In the illustrated embodiment, the passivation layer 226 may be substantially planar. However, in alternative embodiments, the passivation layer 226 may include recesses, such as pits, wells, grooves, and the like. In the illustrated embodiment, the passivation layer 226 has a thickness that is about 150-200 nm and, more particularly, about 170 nm.

The filter layer 224 may include various features that affect the transmission of light. In some embodiments, the filter layer 224 can perform multiple functions. For instance, the filter layer 224 may be configured to (a) filter unwanted light signals, such as light signals from an excitation light source; (b) direct emission signals from the reaction sites toward corresponding sensors 206, 208, 210, 212, and 214 that are configured to detect the emission signals from the reaction sites; or (c) block or prevent detection of unwanted emission signals from adjacent reaction sites. As such, the filter layer 224 may also be referred to as a light-management layer. In the illustrated embodiment, the filter layer 224 has a thickness that is about 1-5 µm and, more particularly, about 2-4 µm. In alternative embodiments, the filter layer 224 may include an array of microlenses or other optical components. Each of the microlenses may be configured to direct emission signals from an associated reaction site to a sensor.

In some embodiments, the solid-state imager 222 and the base substrate 220 may be provided together as a previously constructed solid-state imaging device (e.g., CMOS chip). For example, the base substrate 220 may be a wafer of silicon and the solid-state imager 222 may be mounted thereon. The solid-state imager 222 includes a layer of semiconductor material (e.g., silicon) and the sensors 206, 208, 210, 212, and 214. In the illustrated embodiment, the sensors are photodiodes configured to detect light. In other embodiments, the sensors comprise light detectors. The solid-state imager 222 may be manufactured as a single chip through a CMOS-based fabrication processes.

The solid-state imager 222 may include a dense array of sensors 206, 208, 210, 212, and 214 that are configured to detect activity indicative of a desired reaction from within or along the flow channel 244. In some embodiments, each sensor has a pixel area (or detection area) that is about 1-2 square micrometer (µm²). The array can include 500,000 sensors, 5 million sensors, 10 million sensors, or even 120 million sensors. The sensors 206, 208, 210, 212, and 214 can be configured to detect a predetermined wavelength of light that is indicative of the desired reactions.

In some embodiments, the sampling device 204 includes a microcircuit arrangement, such as the microcircuit arrangement described in U.S. Pat. No. 7,595,882, which is incorporated herein by reference in the entirety. More specifically, the sampling device 204 may comprise an integrated circuit having a planar array of the sensors 206, 208, 210, 212, and 214. The array of the sensors 206, 208, 210, 212, and 214 can be communicatively coupled to a row decoder and a column amplifier or decoder. The column amplifier can also be communicatively coupled to a column analog-to-digital converter (Column ADC/Mux). Other circuitry may be coupled to the above components, including a digital signal processor and memory. Circuitry formed within the sampling device 204 may be configured for at least one of signal amplification, digitization, storage, and processing. The circuitry may collect and analyze the detected fluorescent light and generate pixel signals (or detection signals) for communicating detection data to the signal processor 128. The circuitry may also perform additional analog and/or digital signal processing in the sampling device 204. Sampling device 204 may include conductive vias 230 that perform signal routing (e.g., transmit the pixel signals to the signal processor 128). The pixel signals may also be transmitted through electrical contacts 232 of the sampling device 204.

However, the sampling device 204 is not limited to the above constructions or uses as described above. In alternative embodiments, the sampling device 204 may take other forms. For example, the sampling device 204 may comprise a CCD device, such as a CCD camera, that is coupled to a flow cell or is moved to interface with a flow cell having reaction sites therein. In other embodiments, the sampling device 204 may be a CMOS-fabricated sensor, including chemically sensitive field effect transistors (chemFET), ion-sensitive field effect transistors (ISFET), and/or metal oxide semiconductor field effect transistors (MOSFET). Such embodiments may include an array of field effect transistors (FET's) that may be configured to detect a change in electrical properties within the reaction chambers. For example, the FET's may detect at least one of a presence and concentration change of various analytes. By way of example, the array of FET's may monitor changes in hydrogen ion concentration. Such sampling devices are described in greater detail is U.S. Patent Application Publication No. 2009/0127589, which is incorporated by reference in the entirety for the use of understanding such FET arrays.

FIG. 2 further shows a cross-section of a biosensor 250 that can be used in various embodiments. Biosensor 250 has wells 256, 258, 260, 262, and 264 that can each hold more than one cluster during a base calling cycle (e.g., 2 clusters per well). The sample surface 234 may be substantially planar (not shown.) In the embodiment shown, the sample surface 234 is shaped to define wells (or reaction chambers) in which each well has one or more reaction sites. The wells may be defined by, for example, well walls that effectively separate the reaction site(s) of one well from the reaction site(s) of an adjacent well.

As shown in FIG. 2, the wells 256, 258, 260, 262, and 264 may be distributed in a pattern along the sample surface 234. For example, the wells 256, 258, 260, 262, and 264 may be located in rows and columns along the sample surface 234 in a manner that is similar to a microarray. However, it is understood that various patterns of wells 256, 258, 260, 262, and 264 may be used. In particular embodiments, each of the wells 256, 258, 260, 262, and 264 includes more than one cluster of biomolecules (e.g., oligonucleotides) that are immobilized on the sample surface 234. For example, well 256 holds cluster pair 206AB, well 258 holds cluster pair 208AB, well 260 holds cluster pair 210AB, well 262 holds cluster pair 212AB, and well 264 holds cluster pair 214AB.

The sensors are configured to detect light signals that are emitted from within the wells. In particular embodiments, pixel areas 206', 208', 210', 212', and 214' can be also associated with corresponding wells 256, 258, 260, 262, and 264 on the sample surface 234, such that light emitted from the wells 256, 258, 260, 262, and 264 is received by the associated pixel areas 206', 208', 210', 212', and 214' and captured by the corresponding sensors 206, 208, 210, 212, and 214.

In embodiments, the sample surface 234 has a fixed position relative to the sampling device 204 so that the wells 256, 258, 260, 262, and 264 have known spatial locations relative to at least one predetermined sensor (or pixel). The at least one predetermined sensor detects activity of the desired reactions from the overlying well. As such, the wells 256, 258, 260, 262, and 264 may be assigned to at least one of the sensors 206, 208, 210, 212, and 214. To this end, the circuitry of the sampling device 204 may include kernels that automatically associate pixel signals (or detection signals) provided by predetermined sensors 206, 208, 210, 212, and 214 with the assigned wells 256, 258, 260, 262, and 264. By way of example, when pixel signals are generated by sensor 206, the pixel signals will automatically be associated with the well 256. Such a configuration may facilitate processing and analyzing the detection data. For instance, the pixel signals from one well may automatically be located at a certain position on the array based on row-wise and/or column-wise decoding.

In some embodiments, the sensors (or pixels) are underlying or below the clusters. In other embodiments, the sensors (or pixels) are overlying or on top of the clusters. In yet other embodiments, the sensors (or pixels) are to the side of the clusters (e.g., to the right and/or left).

Multiple Cluster Base Call Per Sensor (or Pixel)

In embodiments, the technology disclosed increases throughput of the biosensor 205 by using pixel signals from fewer sensors (or pixels) than a number of clusters base called in a base calling cycle. In particular embodiments, if the biosensor 200 has N active sensors, then the technology disclosed uses pixel signals from the N active sensors to base call N+M clusters, where M is a positive integer. In embodiments, this is achieved by base calling multiple clusters per sensor (or pixel), as described below.

In embodiments, a sensor (or pixel) on the sample surface 234 is configured to receive light emissions from at least two clusters. In some embodiments, the sensor simultaneously receives the light emissions from the at least two clusters.

In particular embodiments, the intensity of respective light emissions of the two clusters is significantly different such that one of the two clusters is a "bright" cluster and the other is a "dim" cluster. In embodiments, the intensity values vary between base calling cycles and thus the classification of bright and dim can also change between cycles. In other embodiments, a bright cluster is referred to as a "major" or "dominant" cluster and a dim cluster is referred to as a "minor" or "subordinate" cluster. Some examples of intensity value ratios of emissions between bright and dim clusters include 0.55:0.45, 0.60:0.25, 0.65:0.25, 0.70:0.20, 0.75:0.25, 0.80:0.20, 0.85:0.15, 0.90:0.10, and 0.95:0.05.

In yet other embodiments, the at least two clusters are not bright and dim clusters, but instead clusters with different intensities or clusters generating different types of signals.

During each sampling event (e.g., each illumination stage or each image acquisition stage), a signal processor receives a common, single pixel signal for at least two clusters (e.g., both the bright and dim clusters). The common, single pixel generated at each sampling event includes/represents/reflects/carries light emissions/intensity signals/light captured/sensed information for or from the at least two clusters (e.g., both the bright and dim clusters). In other words, the at least two clusters (e.g., both the bright and dim clusters) contribute to the common, single pixel generated at each sampling event. Accordingly, light emissions from the at least two clusters (e.g., both the bright and dim clusters) are detected simultaneously at each sampling event and the common, single pixel reflects light emissions from the at least two clusters (e.g., both the bright and dim clusters).

For example, in FIG. 2, cluster pair 206AB includes two clusters 206A and 206B which share a sensor 206. As such, cluster 206A can be the dim cluster and cluster 206B can be the bright cluster, depending on their respective intensity values. The signal processor then uses a base calling algorithm to classify pixel signals from the bright and dim clusters into one of sixteen distributions, as described below. In particular embodiments, the bright and dim cluster co-occupy a well, such as well 206. Thus, cluster pairing can be defined based on a shared pixel area or a shared well, or both.

Dual Wells Per Sensor (or Pixel)

Figure 3A:
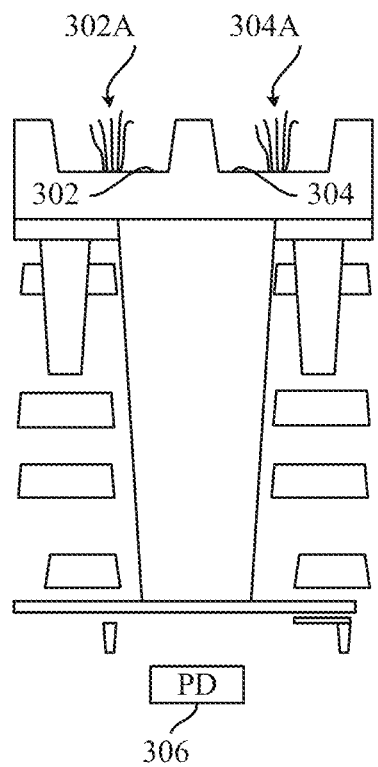
FIG. 3A illustrates a side view of a sample surface having two wells per pixel area including a dominant (or major) well and a subordinate (or minor) well in accordance with one embodiment.
Figure 3B:
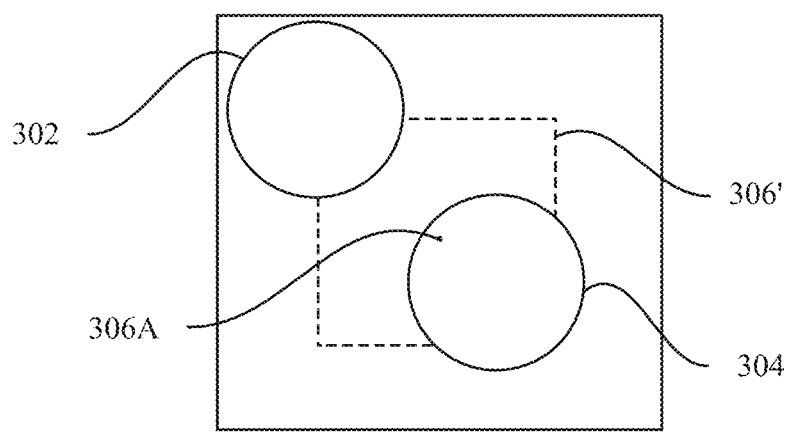
FIG. 3B depicts a top plan view of the sample surface.

FIG. 3A illustrates a side view 300A of a sample surface having two wells per pixel area including a dominant (or major) well and a subordinate (or minor) well in accordance with one embodiment. FIG. 3B depicts a top plan view 300B of the sample surface of FIG. 3A.

In the illustrated embodiment, shared sensor 306 (or pixel) corresponds to two wells 302 and 304 on the sample surface 234. The dominant well has a larger cross section over the pixel area than the subordinate well. Well 304 is the dominant well and well 302 is the subordinate well because well 304 has a larger cross section over the sensor 306.

In embodiments, the two wells have different offsets relative to a center of the pixel area 306'. In the illustrated embodiment, dominant well 304 is more proximate to the pixel area center 306A than the subordinate well 302 (i.e., dominant well 304 has a smaller offset relative to the pixel area center 306A than the subordinate well 302).

Due to the differential cross section coverage and relative offsets result, the sensor 306 receives different amounts of illumination from the two wells during illumination stages of the base calling cycle (or sampling event). Since each of the wells 302 and 304 holds a corresponding cluster 302A and 304A, the different amounts of illumination allow for identification of one of the clusters as bright (or major) and the other as dim (or minor). In the illustrated embodiment, cluster 302A within the dominant well 302 is identified as the bright cluster and cluster 304A within the subordinate well 304 is identified as the dim cluster. In embodiments, sensor 306 receives an amount of illumination from the bright cluster 302A that is greater than an amount of illumination received from the dim cluster 304A in the subordinate well 304.

After the bright and dim clusters are identified, they can be base called by the signal processor 138 using one of the sequencing protocols discussed above. In some dual well per sensor (or pixel) embodiments, the technology disclosed increases throughput of the biosensor 300 by base calling two clusters 302A and 302B held by two corresponding wells 302 and 304 using one shared sensor 306. In other dual well per sensor (or pixel) embodiments, the technology disclosed increases throughput of the biosensor 300 by using N sensors to base call N+M clusters on corresponding N+M wells of the sample surface 234, where M is a positive integer. In some embodiments, M is equal to N or almost equal to N. In other embodiments, M might not be equal to N or even be less than N.

Addressing the Decreasing Signal to Noise Ratio

Figure 4:
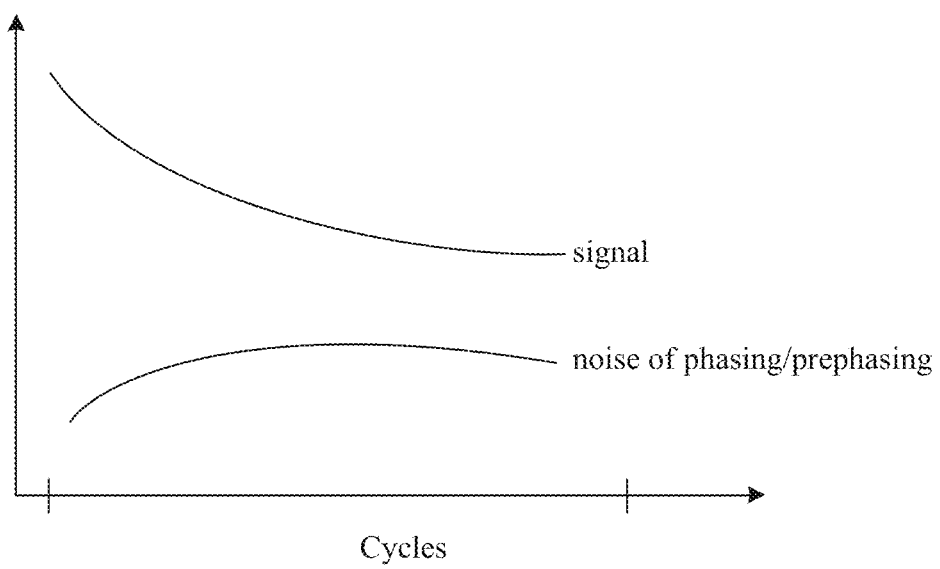
FIG. 4 conceptually illustrates a decreasing signal-to-noise ratio as cycles of sequencing progress.

FIG. 4 conceptually illustrates a decreasing signal-to-noise ratio as cycles of sequencing progress. The top curve illustrates diminishing signal. The bottom curve illustrates an increasing noise floor. The difference between signal in the noise floor decreases, taking with it the signal-to-noise ratio.

We explained above that, for the sensor studied, signal decay results from attaching tags to strands (206A) at positions that are progressively further away from the sensor (206). In addition, phasing and pre-phasing (505) reduce the signal, as they increase the noise.

Phasing and pre-phasing (505) increase noise in successive sequencing cycles, by impacting which tag fluoresces. Phasing and pre-phasing impact which sequence position is tagged and produces light in individual sample strands of an amplified cluster, with a probability distribution represented by the multinomial expansion (513). This distribution broadens as sequencing proceeds.

Decreasing the signal and increasing the noise as cycles progress, as depicted in FIG. 4, reduces the signal-to-noise ratio and complicates base calling.

Figure 5:
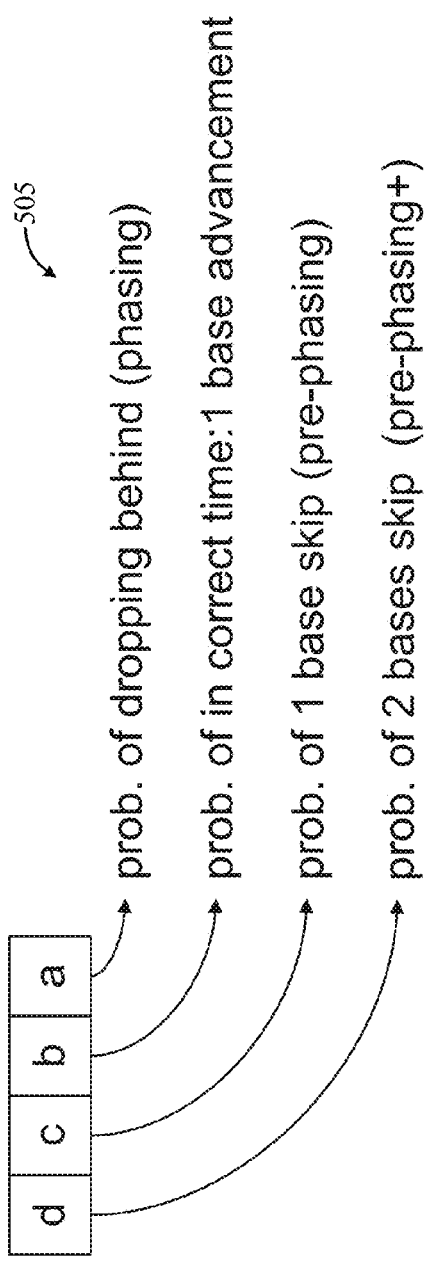
FIG. 5 illustrates use of a convolution kernel to produce an estimated matrix of signal distributions over phasing (behind), in correct time, and pre-phasing (ahead) tag fluorescence.
Figure 5:
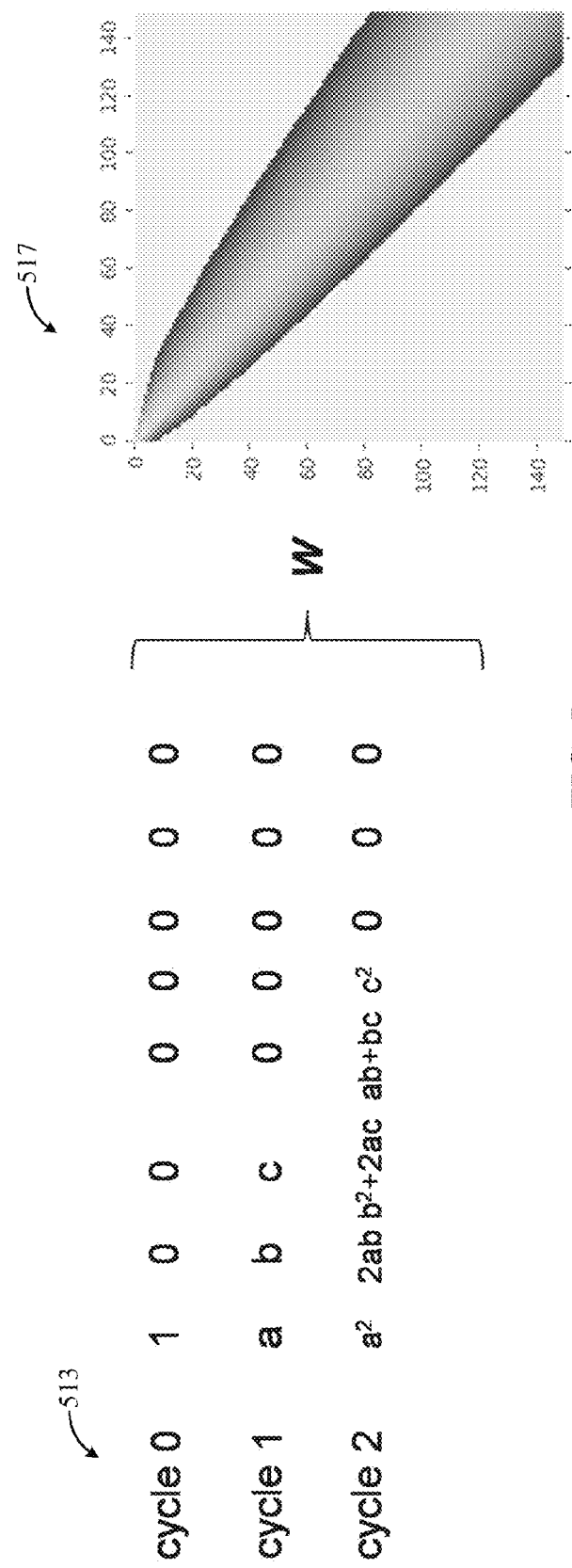
Figure 12:
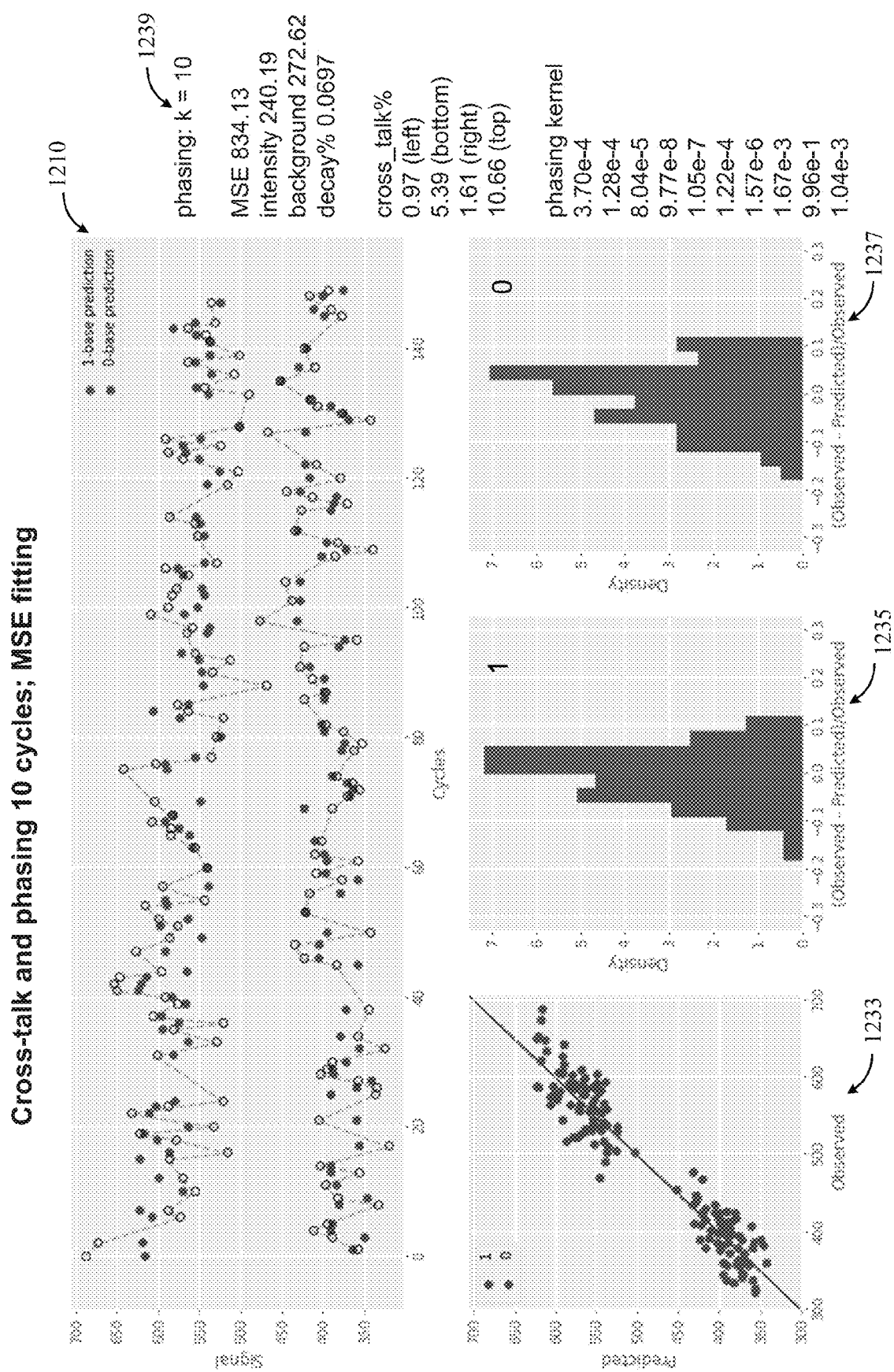

FIG. 5 illustrates use of a convolution kernel to produce an estimated matrix of signal distributions over phasing (behind), in correct time, and pre-phasing (ahead) tag fluorescence. Construction of a four-term polynomial (505) and application of a three-term polynomial (513) are illustrated. Coefficients of the polynomial add up to one or 100%, as the coefficients represent probabilities. Coefficient (a) is the probability that chemical processing during a cycle fails to advance tagging of the sequence. That is, that the nucleotide marked by a fluorescent tag stays in the same location as it was in the prior cycle. The value shown for this event, in FIG. 12, is 0.0017, or 0.17%, which is about 1/600. Coefficient (b) is the dominant probability that the process works as intended and the nucleotide marked by a fluorescent tag advances one location. This outcome has a probability of 99.7%. Coefficient (c) is the probability of pre-phasing and coefficient (d) is the probability of pre-phasing by two positions. Taken together, the probabilities of pre-phasing one or two positions, in FIG. 12, is 0.0012, or 0.12%, which is about 1/800.

The three-term polynomial is applied across cycles 0-2 (513), illustrating how the multi-nominal probability distribution of phasing and pre-phasing broadens as cycles proceed. At cycle 0, it is assumed that the initial attachment of tags is complete. This is a simplification that is useful for illustrative purposes. In cycle 1, the three-term polynomial applies dominant probability (b) that the process will operate correctly and smaller probabilities (a, c) that tagging of any individual strand will fall behind or jump ahead, respectively. In cycle 2, the three-term polynomial is multiplied by itself, producing a second order polynomial with five terms. While the second order polynomial has five terms, the probability of repeated phasing and falling behind by two cycles is only 1/36,000. The probability of repeated pre-phasing and jumping ahead by two cycles is smaller. In cycle 150, repeated multiplication of the three-term polynomial with itself produces a polynomial with 299 terms, with leading and trailing terms of $150^{th}$ order. Since only 150 intensity signals are gathered in this example, terms 151 to 299 can be ignored and not used in the estimated signal distribution matrix W.

Heat map 517 provides a visualization of how the multi-nominal distribution broadens as sequencing cycles progress. The distribution shape resembles a cone.

Figure 6:
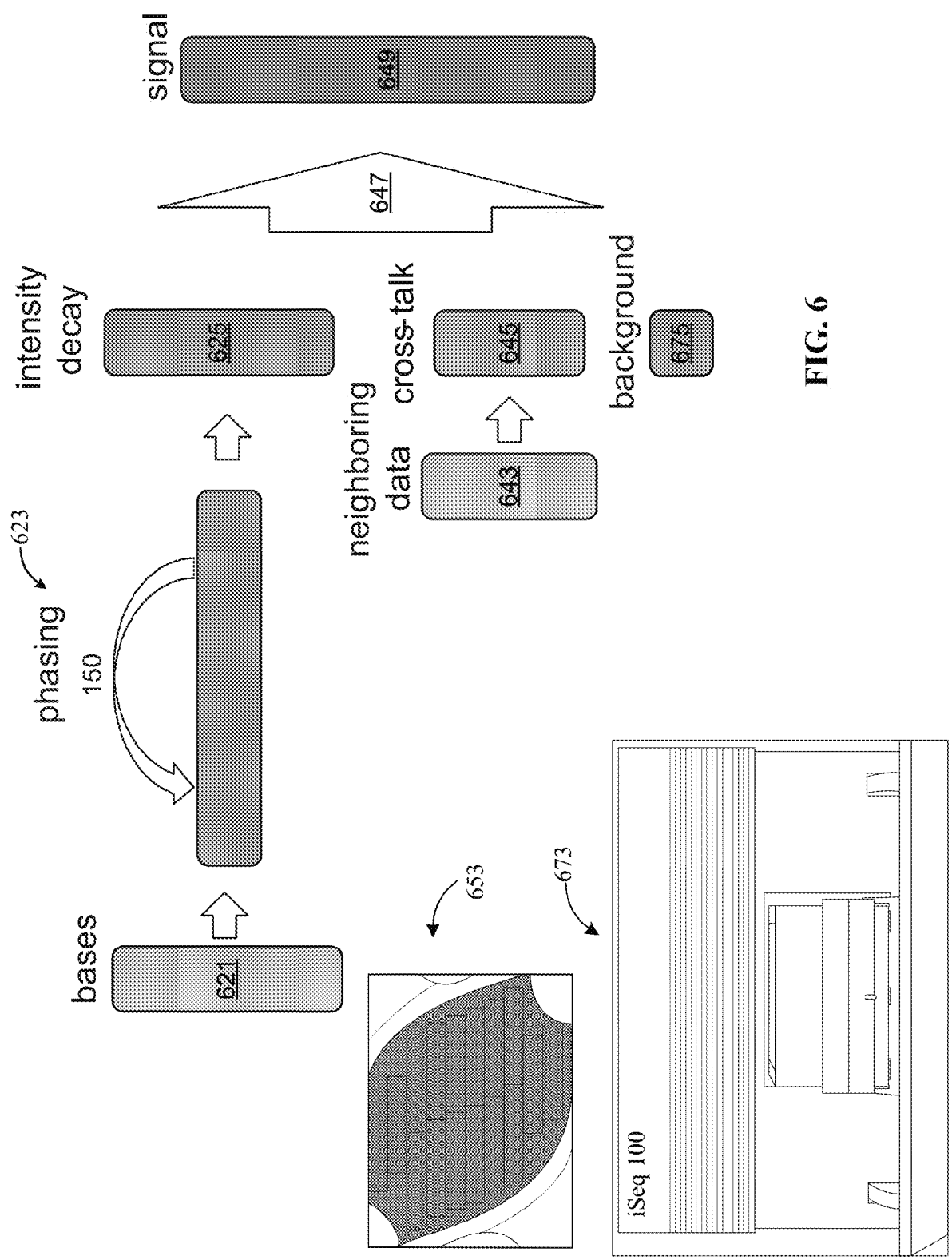
FIG. 6 is a high-level block diagram of deriving actual signals from captured intensity maps, of distinguishing signal from noise.

FIG. 6 is a high-level block diagram of deriving actual signals from captured intensity maps, of distinguishing signal from noise. A sequencing device such as the iSeq 100 (673) uses a flow cell (653), takes intensity readings, and calls bases for clusters on the flow cell. For characterization and performance analysis, the base calling can be against a previously analyzed sample. The ground truth for the sequence of the well-known sample can be in the sequencer base calling and/or prior sequencing of the sample. This ground truth is used when characterizing the sequencer's performance. With this ground truth, intensity data for a particular sensor (621) and neighboring sensors (643) can be corrected to take into account phasing (623), intensity decay (625), crosstalk (645) and background readings (675). The combination of these corrections (647) extracts the underlying signal (649) from captured intensity. In a signal present condition, the extracted signal can be less than half of the captured intensity.

Corrections for phasing (623) and for intensity decay (625) can be calculated for a particular pixel. In our example, 150 intensity the readings are available for the pixel. As sequencing proceeds, phasing and pre-phasing have an increasing impact on whether intensity readings measured are for the current position/cycle or for positions before or after the ideal position for the current cycle. Since intensity readings are available for the entire read, for 150 positions/cycles in this example, data from both prior and subsequent positions can be used to make the phasing correction (623). This correction can be made using a position-dependent 1D convolution. The position-dependent convolutions for the 150 positions can be held in the 150×150 signal distribution estimate matrix W. Similarly, intensity decay (625) can be corrected for the particular pixel, on a position-dependent basis. Factors for intensity decay correction can be held in the 150×1 estimated decay vector d.

Correction for crosstalk (645) depends on intensity readings of neighboring pixels (643). A portion of values from the neighboring intensity readings increases the intensity reading of the particular pixel. Crosstalk coefficients are pixel dependent. While crosstalk is cycle dependent, the dependency relates to intensity in neighboring pixels; the crosstalk coefficients can be calculated once, without dependence on the cycle.

A background intensity level also contributes to the intensity reading for particular pixel. As a first approximation, a general background level can be used. Performance is likely to improve when a particular background level is used for a particular pixel, as will be explained below, in the context of FIGS. 14A-B and 15.

Coefficients for performing these corrections, for instance using the formula above, can be fit by using mean square error as a loss function during gradient descent training. Ground truth for whether a signal is present in a particular intensity channel is available from the base calling of the sample. Coding this truth as a Boolean value multiplicatively injects (1) or removes (0) the signal term for the particular pixel.

Relatively few parameters need to be fit in order to formulate these corrections. In the particular pixel term, the estimated decay vector needs to be fit. After fitting, the only unknown is the underlying signal, which is derived from the other values. In the crosstalk term, for crosstalk coefficients need to be fit taken to account contributions from four neighboring pixels. Alternatively, more coefficients could be used to take into account more neighboring pixels. For instance, if hexagonal pixels were used in the square pixels, crosstalk would come from six neighbors. Or for a patch. Or for a checkerboard patch of nine pixels, all the neighbors could be used. In the background term, a single coefficient can be fit or a coefficient can be fit for each particular pixel. Fitting coefficients for each particular pixel can be based on the individual pixel work and take into account crosstalk from neighboring pixels that may have different background levels. A method is described below for calculating pixel-specific background coefficients that take into account crosstalk from the neighboring pixels. With so few coefficients to fit, gradient descent can calculate the coefficients efficiently. In practice, training benefited from varying the learning rate. Dropout was not required to avoid over fitting.

Relative Contribution of Corrections

Each of the corrections analyzed is valuable by itself. Discussion of their relative value and combined value follows. Residual errors after correction were evaluated and heat maps were generated to confirm the spatial distributions of contributions to intensity the readings. FIGS. 7-12 depict predictions and intensity readings for a sequence of 150 cycles, when various corrections were applied. FIG. 13 illustrates heat maps generated to visualize spatial distribution of contributions by various factors to the measured intensity at individual pixels.

Figure 7:
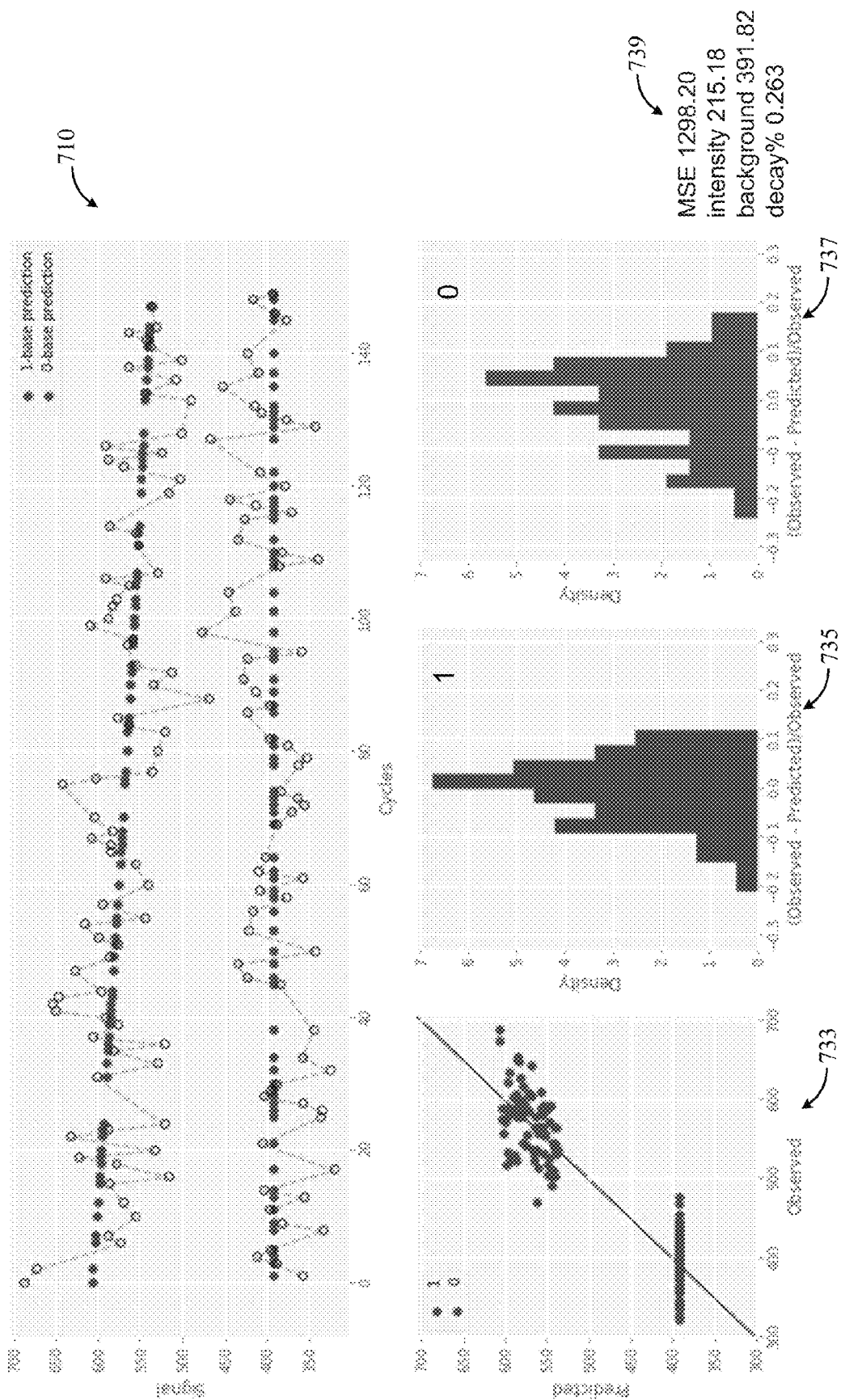
FIG. 7 illustrates analysis of 150 cycles in one run with corrections for just the decay and background.

FIG. 7 illustrates analysis of 150 cycles in one run with corrections for just the decay and background. Note that just one run is shown, one particular pixel. After fitting, the residual mean square error was 1298.20. Predictions represented as solid dots and actual data represented as hollow dots are depicted in the upper panel (710). Predictions are applied to a particular intensity channel for no signal and signal present conditions, ignoring crosstalk and phasing. In lower wine, for the no signal condition, predicted solid dots are at the background level 391.82 (739). Actually readings are scattered above and below the prediction. Residual errors are the difference between predicted and actual values. Gaps in the lower line of solid dots complement solid dots in the upper line. In the upper line, predicting the signal present condition, the solid dots slope downward from 391.82+215.18=607, to approximately 540 at cycle 150 as decay impacts the signal.

Panel 733 is a scatter plot of predicted versus actual or observed values for the clusters of no signal and signal present cycles. Panels 735 and 737 are normalized histograms of residual error between predicted and observed values. panel 735 is for the signal present condition and panel 737 for the no signal condition. Values derived from this characterization (739) include a mean squared error of 1298.20, a background intensity of 391.82, a signal intensity of 215.18 and a per cycle decay of 0.263%.

Figure 8:
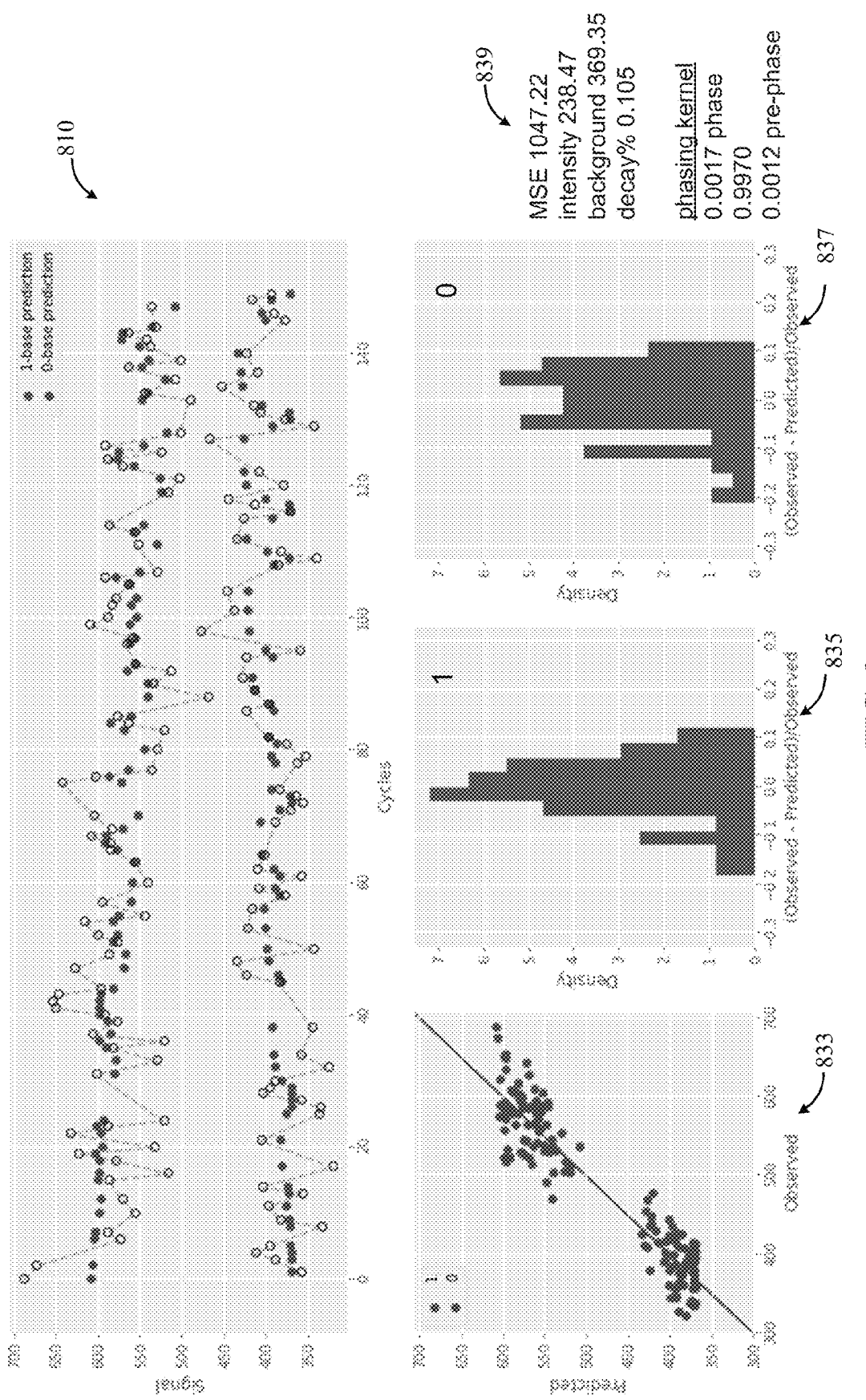
FIG. 8 illustrates analysis of 150 cycles and one run with correction for phasing, in addition to decay and background.

FIG. 8 illustrates analysis of 150 cycles and one run with correction for phasing, in addition to decay and background. Phasing distribution is represented by a three-term polynomial with a single cycle phasing probability of 0.17%, a correct behavior probability of 99.70%, and the pre-phasing probability of 0.12%. After fitting, the residual means where error was reduced to 1047.22. In the top panel 810, predictions and actual values are depicted in solid and hollow dots. The predicted lines are no longer straight. Improvement of the predicted values in following variation of the actual values is sometimes visible. For instance, the predicted no signal condition before and after cycle 100 goes up and down with actual observations. The signal present condition around cycle 80 also has predictions that more closely track observations.

Panel 833 shows a distribution cloud, instead of a constant predicted value of the no signal condition. The distributions in panels 835 and 837 are somewhat tighter than they were without taking into account phasing. Values derived from this characterization (839) include a mean squared error of 1047.22, a reduced background intensity of 369.35, an increased signal intensity of 238.47, with the decreased per cycle decay of 0.105%.

Figure 9:
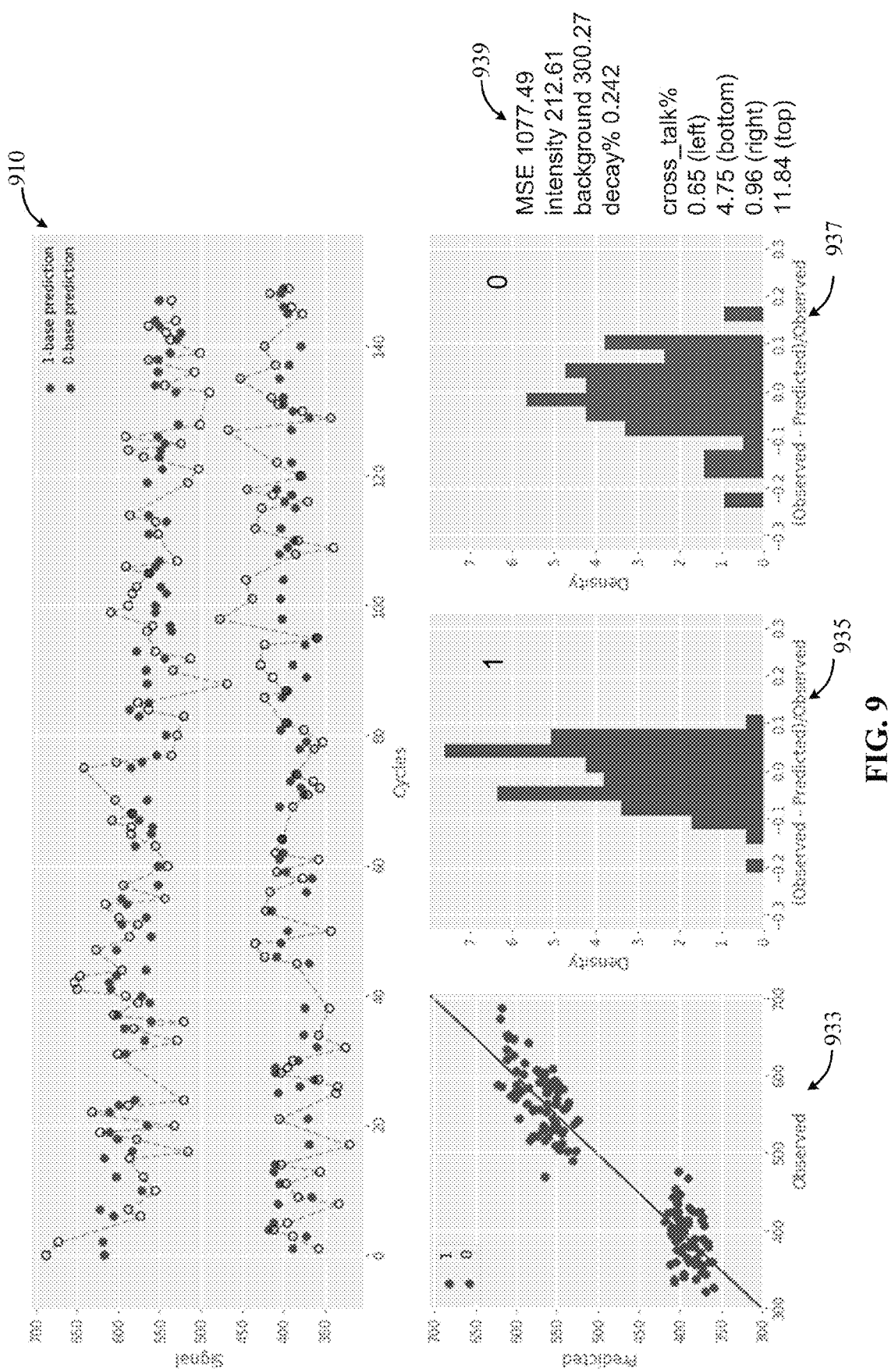
FIG. 9 illustrates analysis of 150 cycles in one run with correction for crosstalk, instead of phasing.

FIG. 9 illustrates analysis of 150 cycles in one run with correction for crosstalk, instead of phasing. Correction for crosstalk did not reduce residual square error as much as correction for phasing. Mean squared residual error was 1077.49. The top panel 810 illustrates that taking into account crosstalk decreased the calculated background to 300.27 with a significant contribution to intensity coming from neighboring pixels.

Panel 933 shows clouds that are rotating to become more aligned to the solid diagonal line. The distributions in panels 935 and 937 have outliers that are not well predicted by correcting for crosstalk. Values derived for this correction (939) include a mean squared error of 1077.49, a reduced background intensity of 300.27, the signal intensity of 212.61 and a per cycle decay of 0.242%. The calculated crosstalk is substantially higher from the top neighboring pixel then from the writer left. Crosstalk coefficients, after fitting, were 11.84% from the top, 4.75% from the bottom, 0.65% from the left and 0.96% from the right.

Figure 10:
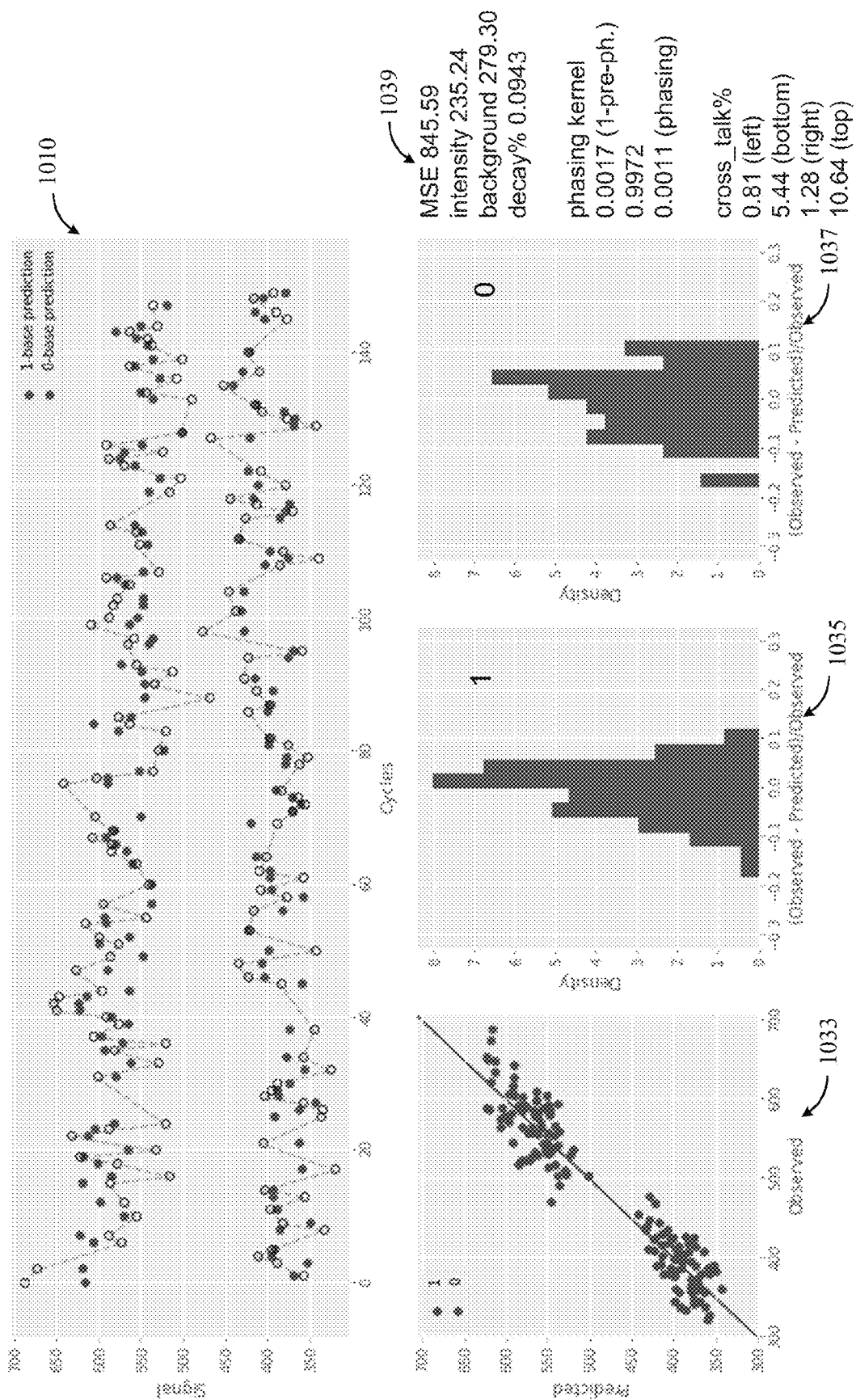
FIG. 10 illustrates combining correction for phasing in crosstalk in addition to estimation of background, intensity and decay.

FIG. 10 illustrates combining correction for phasing in crosstalk in addition to estimation of background, intensity and decay. Correction for both phasing and crosstalk significantly reduced the residual mean square error to 845.59, applying the same three-term polynomial phasing kernel as in FIG. 8. In the top panel 810, predictions go up and down with actual observations especially after cycle 40 with very little overshoot in the predictions.

Panel 1033 shows clouds that are nicely scattered around the solid diagonal line. Residual error history in panels 1035 and 1037 are increasingly tight distributions with some SKU in the no signal prediction due to an outlier. The outliers of lower predicted then observed values can be seen just after cycle 20, just before cycle 100 and just before cycle 130. Values drive for this correction (1039) include a mean squared error of 845.59, a lower background of 279.30, the signal intensity of 235.24 and a reduced decay per cycle of 0.0943%. The crosstalk coefficients show a decrease in crosstalk from the top and slight increases from other neighboring pixels. Crosstalk coefficients were 10.64% from the top, 5.44% from the bottom, 0.81% from the left and 1.28% from the right.

Figure 11:
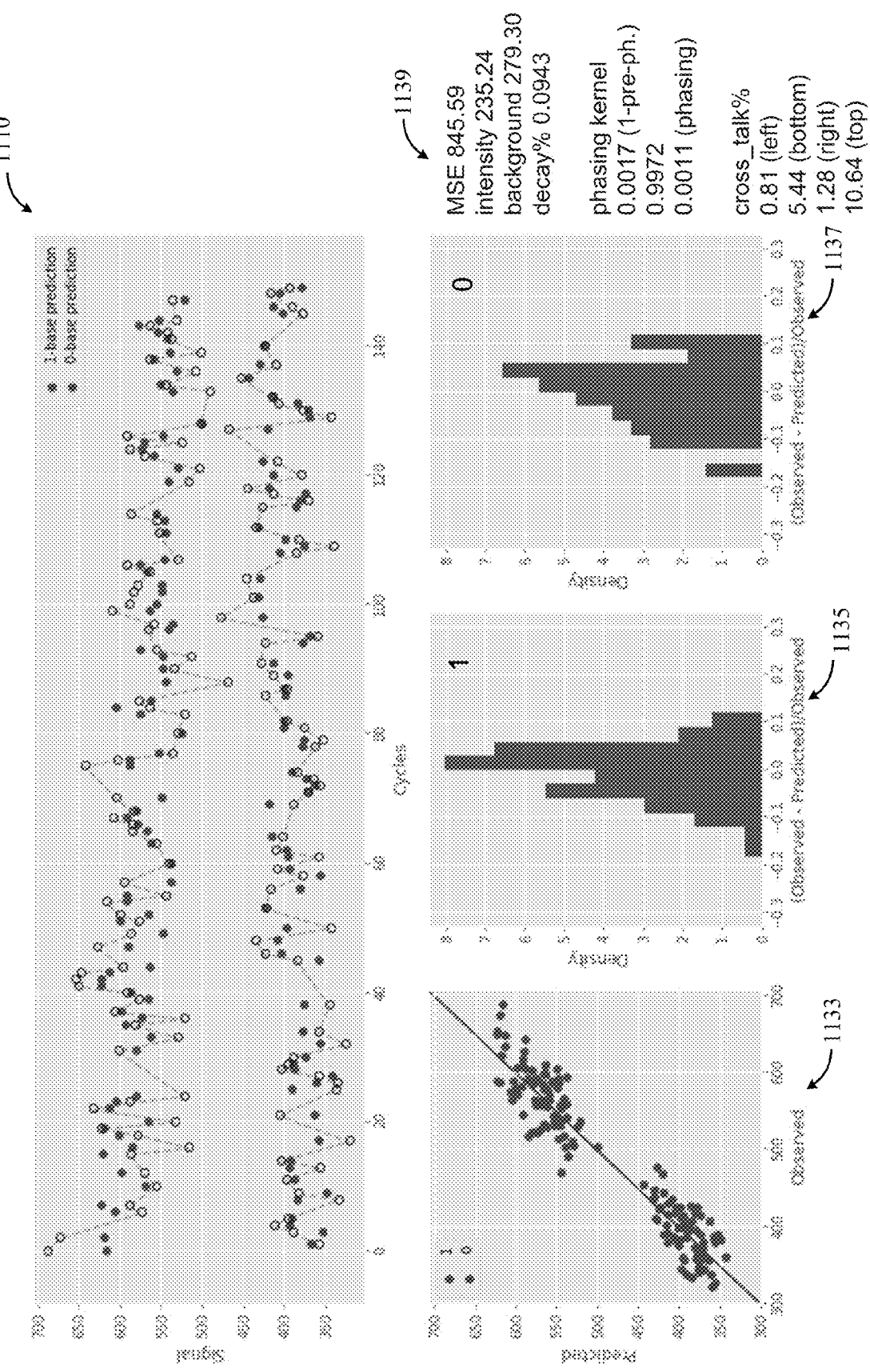
FIGS. 11 and 12 analyze using expanded phasing kernels, expanded to five- and ten-term polynomials that handle up to 3 and 8 pre-phasing skips, respectively.

FIGS. 11 and 12 analyze using expanded phasing kernels, expanded to five- and ten-term polynomials. FIG. 11 illustrates expanding the phasing kernel from 3 to 5 cycles, covering pre-phasing by up to three skips. Expansion of the phasing kernel increases the number of pre-phasing forward skips accounted for in a particular cycle; in contrast, phasing can only result in falling behind by one position per cycle, so the number of phasing coefficients remains one. Increased correction for pre-phasing from one to three skips only reduced the mean squared error from 845.59 to 844.04, which produces very little change in any of the visualization panels between FIGS. 10 and 11. Small improvements in background, intensity and per cycle decay resulted. Calculated crosstalk from top and right pixels increased marginally while crosstalk from bottom and left pixels was unchanged.

FIG. 12 illustrates expanding the phasing kernel further to 10 cycles, covering up to eight skips. The probability of correct tagging performance is slightly reduced in this kernel from 99.70% to 99.6%. This extreme correction for pre-phasing only reduced the mean squared error to 834.13. Background slightly decreased, intensity slightly increased and decay slightly decreased. The most apparent feature among the visualization panels is in 1237, where two-thirds of the low outlier points from panel 1137 are brought closer to the center of the distribution.

Figure 13B:
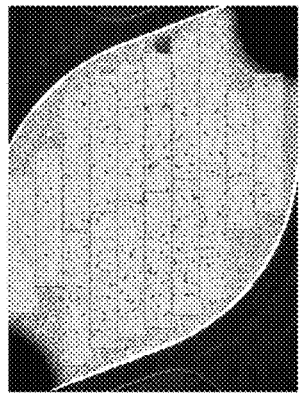
Figure 13C:
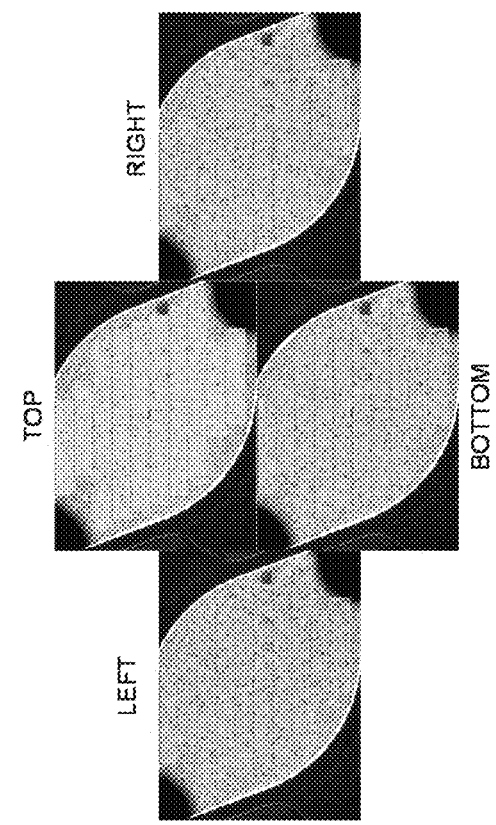
Figure 13F:
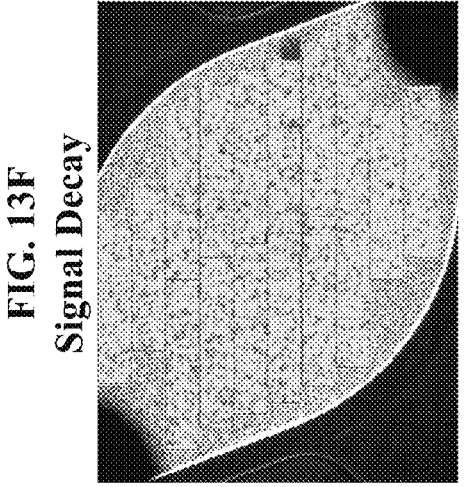
Figure 13E:
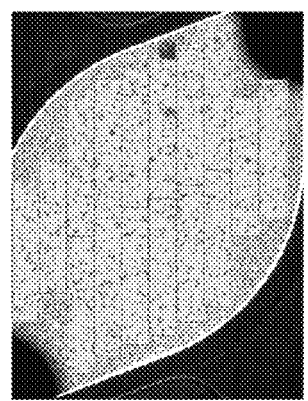
Figure 13D:
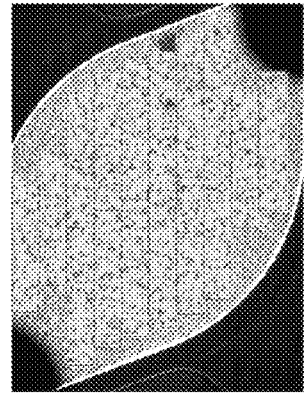

FIGS. 13A-F are a series of heat maps created by applying false color to a photograph of a flow cell, based on analysis of contributions of various factors to measured intensities in an intensity map for one channel. The factors analyzed and visualized are contributions of background illumination (FIG. 13A), background sensor variation (FIG. 13B), cross talk from neighboring pixels (FIG. 13C), phasing and pre-phasing (FIGS. 13D-E), and signal decay (FIG. 13F). Over 150 cycles, parameters were separately calculated for each pixel.

The phasing, pre-phasing and signal decay maps indicate uniform distributions of variation. For instance, the visualization of signal decay (FIG. 13F) does not show any apparent pattern, except at the exit from the flow cell in the bottom right corner. This exit area shows variation in all of the heat maps. Heat maps for phasing and pre-phasing (FIGS. 13D-E) also have uniform distributions, excepting a red colorized splotch just to the left of the dark, uncolorized splotch, five rows from the bottom. A difference in color between the phasing and pre-phasing in the heat maps indicates that phasing is slightly more likely than pre-phasing. The uniform distributions in heat maps indicate random variations of several factors during sequencing, as expected.

FIG. 13A-B separate background illumination effects from sensor-specific background reading biases. The background illumination heat map (FIG. 13A) indicates brighter illumination on the left side of the flow cell than on the right side. Apart from illumination effects, the sensor-specific biases on background readings is mapped in FIG. 13B. This apparent manufacturing or design artifact was larger than expected, as discussed below in the context of FIGS. 14A-B.

FIG. 13C maps relative crosstalk contributions of top, bottom, left and right adjoining pixels. The largest contributor by far is the top pixel, located north of the center pixel that is generating a signal. The bottom pixel contributes more crosstalk than either left or right neighboring pixels. (However, analysis below suggests that this estimation may be biased.)

For manufacturing and design, these heat maps characterize performance of this particular flow cell in a way that suggests design and manufacturing improvements. Illumination is not quite uniform, could be improved. Systematically greater crosstalk from the top and bottom pixels suggests potential design or manufacturing improvement, or could simply be a consequence of asymmetry in placement of dominant and secondary wells in a dual well design (300B). The red colorized splotch just to the left of the dark, uncolorized splotch, five rows from the bottom, suggests a manufacturing defect to be investigated by deconstruction of this particular flow cell. The red colorized splotch at the outlet of the flow cell, in the bottom right corner, may indicate an opportunity for design improvement. Thus, characterization of flow cell performance leads to manufacturing and design improvements.

For inference and base calling during production, these heat maps confirm the coefficients derived and general applicability of the corrections identified. Accurate identification of factors to be corrected leads to informed design of inputs to and structure of a deep learning system.

FIGS. 14A-B reflect sensor-specific variation in background readings that is not randomly distributed. The 2d histogram in FIG. 14A revealed that there are background reading levels for the no signal condition in three ranges, around 250, 750 and 900, as indicated by arrows. The std histogram in FIG. 14B confirmed three distinct background levels, in steps to the left of the vertical dashed line. As an improvement to the model, individual pixel background levels were set, instead of having a uniform sensor background reading.

FIG. 15 presents a background level hyper-parameter approach to setting a particular pixel's background level taking into account background levels of its neighbors. A subject of analysis in FIG. 15 is whether to adjust a pixel level by its minimum background level in the no signal condition or by slightly less than the minimum background level. One approach to shifting the signal level of a particular pixel would be to subtract the minimum signal level for that pixel (in that intensity channel) over the cycles measured. A minimum signal level corresponds to the no signal condition, as opposed to the signal present condition. It is intuitively appealing to subtract the full minimum value, but analysis showed that subtracting somewhat less produced better corrections. Graph 1513 shows measured intensity values for both no signal and signal present conditions for a particular pixel, in red, and values of four neighboring pixels, in blue. The particular pixel was selected because neighboring pixels included clusters. For each of the five pixels, there are distinct lines for no signal and signal present conditions. However, these distinct lines are relatively close together in graph 1531 and not visually distinguishable for the neighboring pixels.

Graph 1515 depicts the effect on mean squared error of adjusting intensity values by 90 to 100% of the minimum intensity value for the particular pixel. As expected, adjusting individual pixels by subtracting increasing portions of their minimum background level improves the mean squared error. Surprisingly, the improvement stops at 99% of the minimum intensity value and turns back upward when 100% of the minimum intensity value is used as an adjustment factor. This observation can be tested by creating a free parameter, shrinkage_limit:

Shifted_signals=signals−(min(signals)*
shrinkage_limit), where signals is a vector of measured intensities of a pixel in a channel,
min(signals) is the minimum value in the vector, and
shrinkage_limit is a hyper parameter typically in a range of 0.90 to 1.00.

In this example, analysis of mean square errors for small variations in the shrinkage_limit hyper parameter revealed a best correction at 0.99.

Graph 1517 shows distributions of pixel intensity readings, reduced by 0.99*min(signals) for the five pixels, plotted on a rescaled graph. Instead of a plot over the intensity level range from 0 to 1000, this graph, after adjustment, plots intensity levels over a range from 0 to 225. Upper sequences of dots, for the signal present condition, are visually separated from lower sequences of dots, for the no signal condition. In tables 1521 and 1527, estimated mean squared error reportedly was substantially reduced and bias removed from crosstalk estimations. The mean squared error was reduced from 82.85 to 57.54. The big reduction in mean squared error resulted from pixel-by-pixel adjustment to remove a large portion of background from the intensity readings.

At this pixel location, tables 1521 and 1527 indicate that crosstalk from the top pixel was not dominant. Removal of bias produced an estimate that crosstalk from neighbors was nearly equal. This is less suggestive of a manufacturing or illumination angle issue than appeared from the crosstalk coefficients of FIGS. 7-13. In tables 1523 and 1529, parameters for the center or red pixel, before and after adjustment, are given.

While the intensity signal dropped somewhat, it is no longer a small proportion of the background level. The decay estimation increased slightly. The phasing and prephasing estimations decreased slightly.

FIG. 16 includes tables that illustrate reduced estimates of crosstalk after accounting for multiple background levels intrinsic to individual sensors. The tables include data for median values of crosstalk coefficients among pixels whose neighbors include DNA clusters. Two intensity channels, for red and green laser illumination, are indicated for three different flow cells. Crosstalk coefficients for top, bottom, left and right neighbors are given. After adjustment, estimated crosstalk coefficients were half or less of the originally estimated coefficients. For the pixels analyzed, adjustment based on intrinsic background levels of sensors eliminated the appearance that crosstalk from the top neighbor dominated crosstalk from other neighbors, which appeared in FIGS. 7-13.

Figure 18:
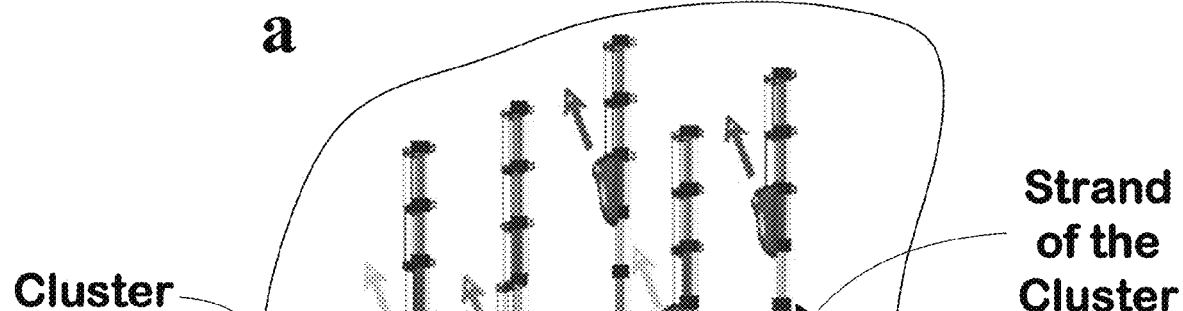
FIG. 18 illustrates one example of the phasing and pre-phasing effect.
Figure 18:
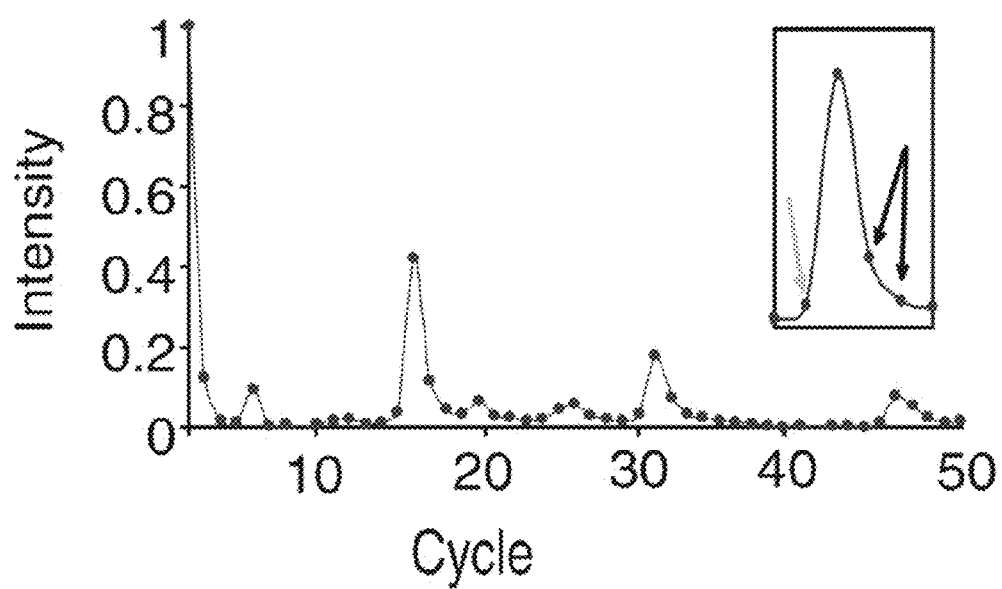

FIG. 18 illustrates one example of the phasing and prephasing effect.

Figure 19:
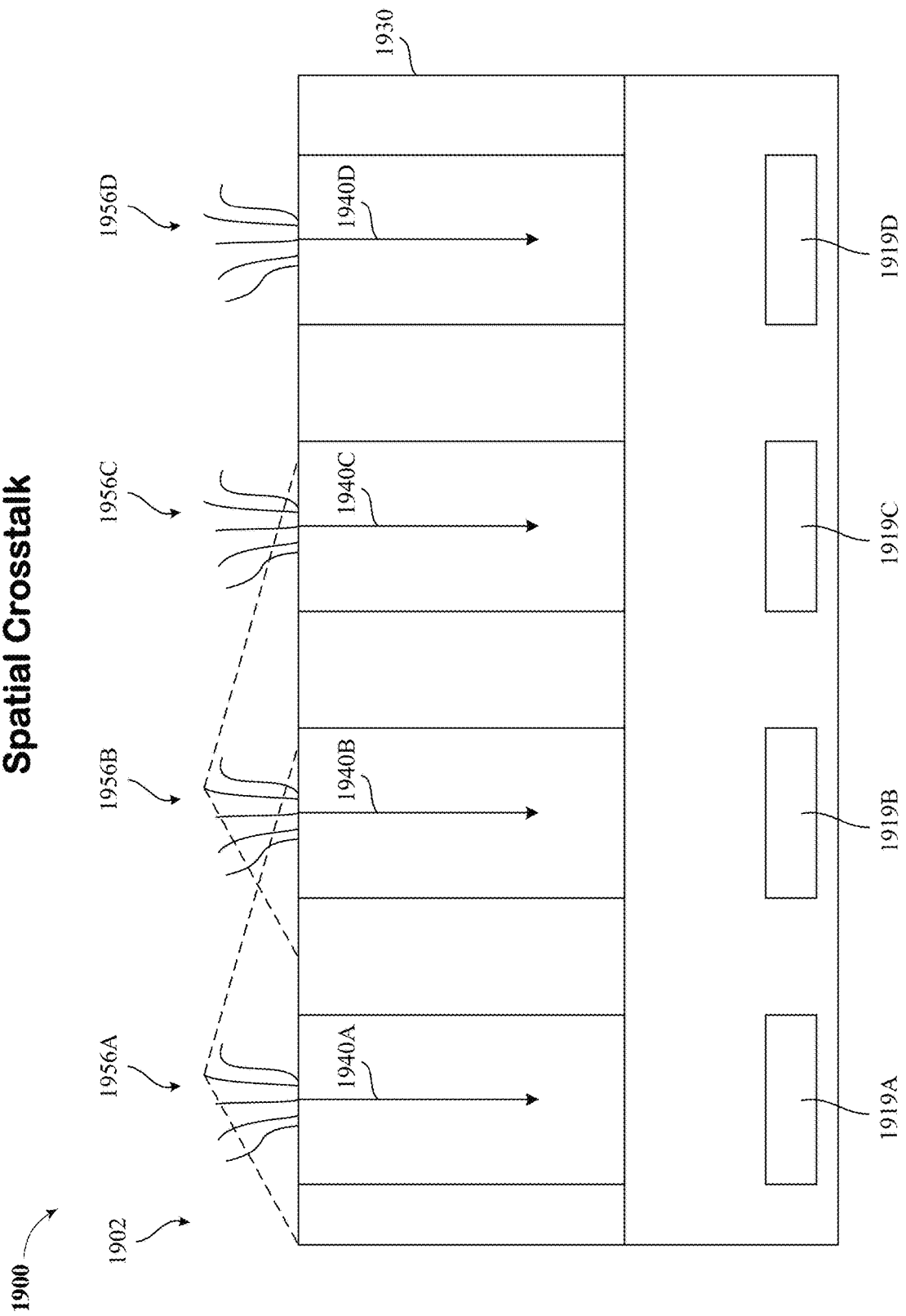
FIG. 19 illustrates one example of spatial crosstalk.

FIG. 19 illustrates one example of spatial crosstalk.

Figure 20:
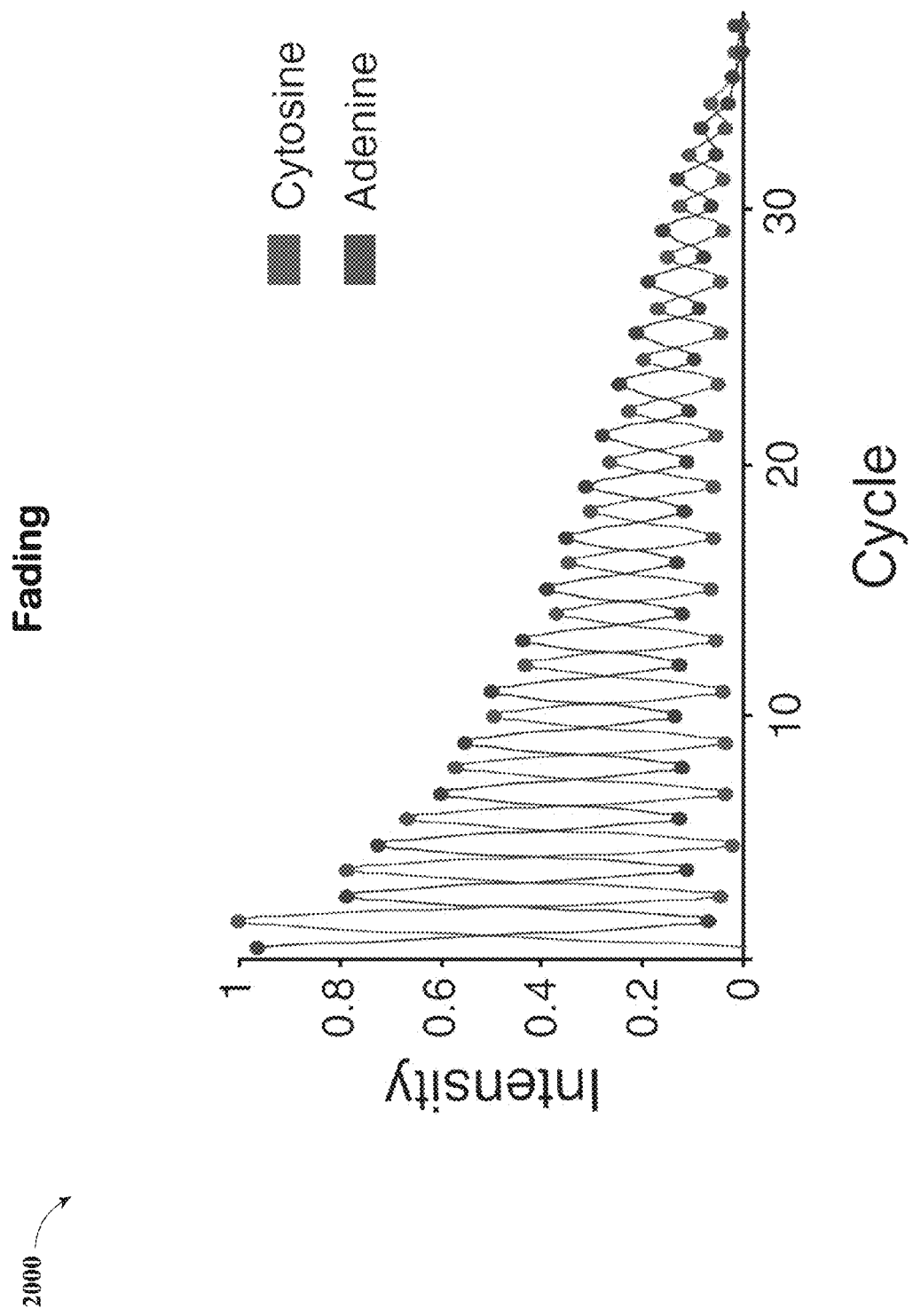
FIG. 20 illustrates one example of fading.

FIG. 20 illustrates one example of emission overlap.

Figure 21:
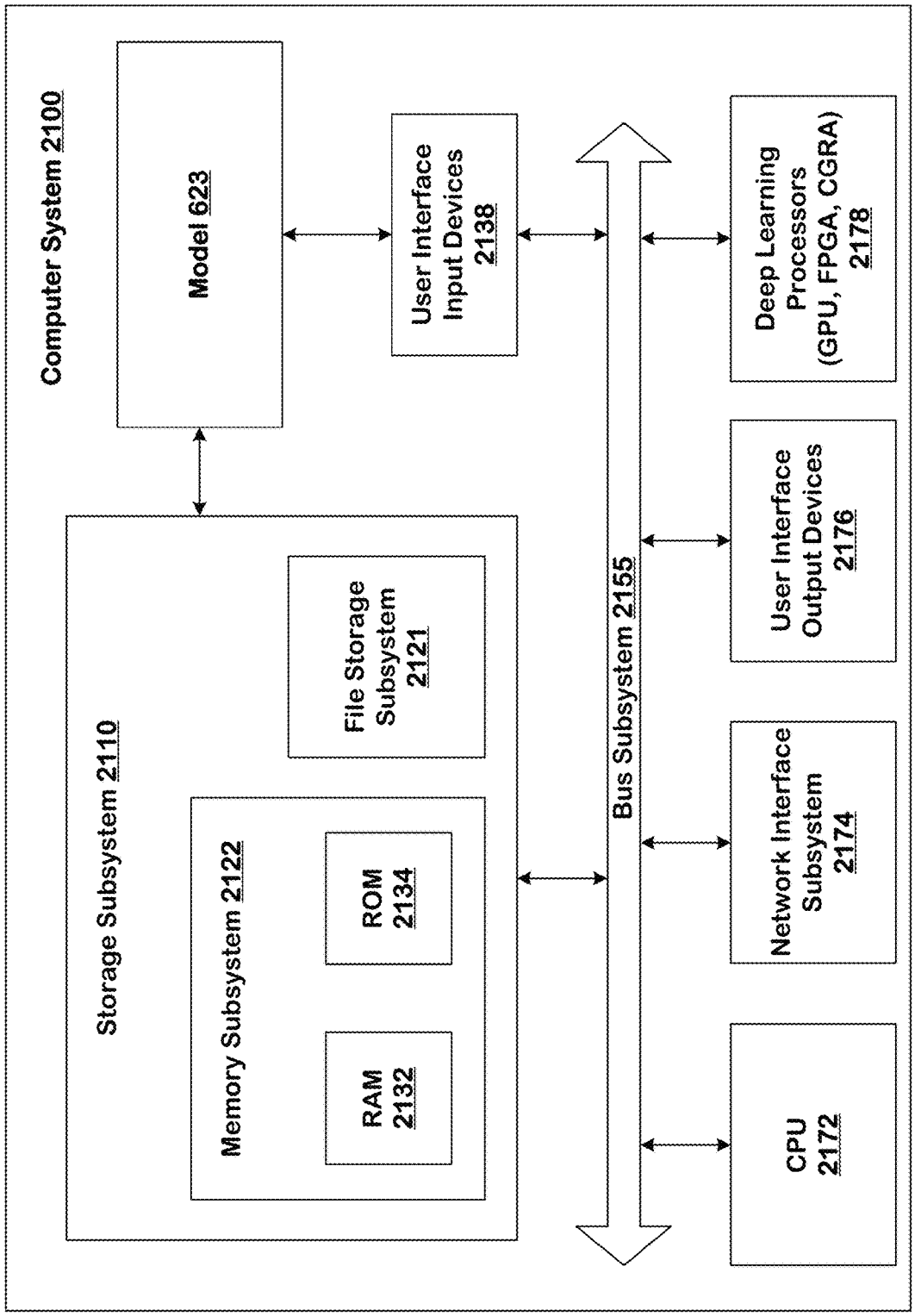
FIG. 21 is a computer system that can be used to implement the technology disclosed.

FIG. 21 illustrates one example of fading.

FIG. 22 is a computer system that can be used to implement the technology disclosed.

In the ideal situation, the lengths of all nascent strands within an analyte would be the same. Imperfections in the cyclic reversible termination (CRT) chemistry create stochastic failures that result in nascent strand length heterogeneity, introducing lagging (too short) and leading (too long) nascent strands within the analyte and reduces the purity of signal output from the interrogated position by contamination with signals from adjacent nucleotides. Phasing and prephasing effect refers to contamination of the signal for a specific cycle by the signal of the cycles before and after. Phasing and pre-phasing leads to the loss of synchrony in the readout of the sequence copies of an analyte.

Phasing is caused by incomplete removal of the 3' terminators and fluorophores as well as sequences in the analyte missing an incorporation cycle. Prephasing is caused by the incorporation of nucleotides without effective 3'-blocking. Phasing and prephasing effect is a nonstationary distortion and thus the proportion of sequences in each analyte that are affected by phasing and prephasing increases with cycle number; hampering correct base identification and limiting the length of useful sequence reads.

Incomplete extension due to phasing results in lagging strands (e.g., t−1 from the current cycle). Addition of multiple nucleotides or probes in a population of identical strands due to prephasing results in leading strands (e.g., t+1 from the current cycle). Other terms used to refer to phasing and phasing include falling behind, moved ahead, lagging, leading, dephasing, post-phasing, out-of-phase, out-of-sync, out-of-step nucleotide synthesis, asynchronicity, carry-forward (CF), incomplete or premature extension (IE), and droop (DR).

FIG. 18 illustrates one example of the phasing and prephasing effect 1800. FIG. 18*a* shows that some strands of an analyte lead (red) while others lag behind (blue), leading to a mixed signal readout of the analyte. FIG. 18*b* depicts the intensity output of analyte fragments with "C" impulses every 15 cycles in a heterogeneous background. Notice the anticipatory signals (gray arrow) and memory signals (black arrows) due to the phasing and prephasing effect 1800.

Spatial crosstalk refers to a signal or light emission from one or more non-associated analytes (or pixel areas) that is detected by a corresponding light detector of an associated analyte (or pixel area). Spatial crosstalk is caused by unwanted emissions from adjacent analytes. Ideally, the intensities of each analyte should correspond to just one analyte sequence. However, the observed intensities often contain signals from neighboring analyte sequences, other than the interrogated/target one, and, hence, are not pure.

FIG. 19 illustrates one example of spatial crosstalk. FIG. 19 illustrates a detection device 1900 having a plurality of pixel areas 1956A-1956D on a detector surface 602. The detection device 1900 includes light sensors 1919A-1919D. The light sensors 1919A-1919D are associated with and correspond to the pixel areas 1956A-1956D, respectively. Corresponding detection paths 1940A-1940D extend between the light sensors 1919A-1919D and corresponding pixel areas 1956A-1956D. The arrows that indicate the detection paths 1940A-1940D are merely to illustrate a general direction that the light propagates through the respective detection path.

During an imaging event, the detection device 1900 is configured to detect light using the light sensors 1919A-1919D. As demonstrated in FIG. 19 by pyramidal hash marked areas or zones, light emissions (or emission signals) are propagating from the pixel areas 1956A and 1956B, but light emissions are not propagating from 1956C or 1956D. The light emissions may be indicative of, for example, a positive binding event between the analytes located at the corresponding pixel area and another biomolecule. In particular implementations, the pixel areas 1956A-1956D are illuminated by an excitation light (e.g., 532 nm). The pixel areas 1956A and 1956B are bound to respective biomolecules having light labels (e.g., fluorescent moieties). In response to the excitation stimulus, the pixel areas 1956A and 1956B provide light emissions as demonstrated in FIG. 19.

However, the pixel areas 1956 and the light sensors 1919 may be located relatively close to one another such that light emissions from a non-associated pixel area may be detected by a light sensor. Such light emissions may be referred to as crosstalk emissions or spatial crosstalk. By way of example, the light emissions propagating from the pixel area 1956A include a crosstalk signal and a pixel signal. The pixel signal of the light emissions from the pixel area 1956A is that signal of the light emissions that is configured to be detected by the light sensor 1919A. In other words, the pixel signal includes the light emissions that propagate at an angle that is generally toward the light sensor 1919A such that filter walls 1930 defining the detection path 1940A are capable of directing the light emissions toward the light sensor 1919A. The crosstalk signal is that signal of the light emissions that clears the filter walls 1930 defining the detection path 1940A and propagates into, for example, the detection path 1940B. In such cases, the crosstalk signal may be directed to the light sensor 1919B, which is not associated with the pixel area 1956A. Thus, the light sensor 1919B may be referred to as a non-associated light sensor with respect to the pixel area 1956A.

Using the implementation shown in FIG. 19 as an example, the light sensor 1919A may detect the pixel emissions from the pixel area 1956A and the crosstalk emissions from the pixel area 1956B. Likewise, the light sensor 1919B may detect the pixel emissions from the pixel area 1956B and the crosstalk emissions from the pixel area 1956A. The light sensor 1919C may detect the crosstalk emissions from the pixel area 1956B. However, the pixel area 1956C is not providing light emissions in FIG. 19. Thus, an amount of light detected by the light sensor 1919C is less than the corresponding amounts of light detected by the light sensors 1919A and 1919B. As shown in FIG. 19, the light sensor 1919C only detects crosstalk emissions from the pixel area 1956B, and the light sensor 1919D does not detect crosstalk emissions or pixel emissions.

Fading is an exponential decay in fluorescent signal intensity as a function of cycle number. As the sequencing run progress, the analyte strands are washed excessively, exposed to laser emissions that create reactive species, and subject to harsh environmental conditions. All of these lead to a gradual loss of fragments in each analyte, decreasing its fluorescent signal intensity. Fading is also called dimming or signal decay. FIG. 20 illustrates one example of fading 2000. In FIG. 20, the intensity values of analyte fragments with AC microsatellites show exponential decay.

Computer System

FIG. 21 is a computer system 2100 that can be used to implement the convolution-based base calling and the compact convolution-based base calling disclosed herein. Computer system 2100 includes at least one central processing unit (CPU) 2172 that communicates with a number of peripheral devices via bus subsystem 2155. These peripheral devices can include a storage subsystem 2110 including, for example, memory devices and a file storage subsystem 2121, user interface input devices 2138, user interface output devices 2176, and a network interface subsystem 2174. The input and output devices allow user interaction with computer system 2100. Network interface subsystem 2174 provides an interface to outside networks, including an interface to corresponding interface devices in other computer systems.

In one implementation, the model 623 is communicably linked to the storage subsystem 2110 and the user interface input devices 2138.

User interface input devices 2138 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 2100.

User interface output devices 2176 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 2100 to the user or to another machine or computer system.

Storage subsystem 2110 stores programming and data constructs that provide the functionality of some or all of the modules and methods described herein. These software modules are generally executed by deep learning processors 2178.

Deep learning processors 2178 can be graphics processing units (GPUs), field-programmable gate arrays (FPGAs), application-specific integrated circuits (ASICs), and/or coarse-grained reconfigurable architectures (CGRAs). Deep learning processors 2178 can be hosted by a deep learning cloud platform such as Google Cloud Platform™ Xilinx™, and Cirrascale™. Examples of deep learning processors 2178 include Google's Tensor Processing Unit (TPU)™, rackmount solutions like GX4 Rackmount Series™ GX21 Rackmount Series™, NVIDIA DGX-1™, Microsoft' Stratix V FPGA™ Graphcore's Intelligent Processor Unit (IPU)™, Qualcomm's Zeroth Platform™ with Snapdragon Processors™, NVIDIA's Volta™, NVIDIA's DRIVE PX™, NVIDIA's JETSON TX1/TX2 MODULE™, Intel's Nirvana™, Movidius VPU™, Fujitsu DPI™ ARM's DynamicIQ™, IBM TrueNorth™, and others.

Memory subsystem 2122 used in the storage subsystem 2110 can include a number of memories including a main random access memory (RAM) 2132 for storage of instructions and data during program execution and a read only memory (ROM) 2121 in which fixed instructions are stored. A file storage subsystem 2121 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 2121 in the storage subsystem 2110, or in other machines accessible by the processor.

Bus subsystem 2155 provides a mechanism for letting the various components and subsystems of computer system 2100 communicate with each other as intended. Although bus subsystem 2155 is shown schematically as a single bus, alternative implementations of the bus subsystem can use multiple busses.

Computer system 2100 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 2100 depicted in FIG. 21 is intended only as a specific example for purposes of illustrating the preferred implementations of the present invention. Many other configurations of computer system 2100 are possible having more or less components than the computer system depicted in FIG. 21.

Particular Implementations

We describe various implementations of determining tag signals from measured intensities. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

In one implementation, we disclose a computer-implemented method of determining tag signals from measured intensities. The measured intensities are collected by light sensors in a sensor array directed to a sample surface. The sample surface include pixel areas and hold a plurality of clusters during a sequence of sampling events. Each light sensor is directed to and measures intensity from one of the pixel areas during each sampling period.

An adjustment determiner 1702 determines an adjustment to the measured intensities from a pixel in the sampling periods for crosstalk from neighboring pixels by applying crosstalk estimations to measured intensities of the neighboring pixels in respective sampling periods.

The adjustment determiner 1702 determines a further adjustment to the measured intensities from the pixel in the sampling periods for background intensity.

The tag signals determiner 1704 determines the tag signals originating from the pixel in the sampling periods, takes into account the adjustment and the further adjustment to the measured intensities, combined with modifying at least the measured intensities to take into account signal decay over progress of the sequence and for phasing and pre-phasing.

The intensity modifier 1712 modifies the measured intensities in the sampling periods by a progressive decay function that takes into account how late each sampling period occurs in the sequence.

The distribution function applier 1712 applies a distribution function to at least current, prior and subsequent measured intensities, uses signal presence ground truth for the pixel in the sampling periods, and separates intensity contributions due to phasing and pre-phasing from contribution of a current tag signal to the current measured intensity.

The method described in this section and other sections of the technology disclosed can include one or more of the following features and/or features described in connection with additional methods disclosed. In the interest of conciseness, the combinations of features disclosed in this application are not individually enumerated and are not repeated with each base set of features. The reader will understand how features identified in these implementations can readily be combined with sets of base features identified in other implementations.

In one implementation, the distribution function for phasing and pre-phasing takes into account a broadening distribution over progress of the sequence. In one implementation, the broadening distribution is determined by repeatedly convolving a phasing kernel with itself.

In one implementation, the phasing kernel includes three terms for probabilities of sequence processing advancing as intended, failing to advance and skipping ahead by one position. In one implementation, the phasing kernel includes five terms for probabilities of sequence processing advancing as intended, failing to advance, skipping ahead by one position, skipping ahead by two positions, and skipping ahead by three positions.

In one implementation, the decay function is an exponential decay. In one implementation, the adjustment for background intensity is performed for the pixel using pixel-by-pixel background coefficients.

In one implementation, the adjustment for background intensity is a proportion between 0.95 and 0.995 of a minimum measured intensity for the pixel over the measured intensities in the sequence. In one implementation, the proportion is determined taking into account interaction between crosstalk from the neighboring pixels and the background adjustment for the pixel and the neighboring pixels.

In one implementation, the adjustment for crosstalk is performed for the pixel using a pixel-by-pixel crosstalk coefficients. In some implementations, a coefficients determiner 1722 determines coefficients for the crosstalk estimation and coefficients for the background intensity and coefficients for the decay function and coefficients for the distribution function by applying gradient descent to the signal presence ground truth for the pixel and the measured intensities for the sequence of the sampling events for the pixel.

In one implementation, the sampling events are applied to a known sample and the signal presence ground truth is based on reliable sequencing of the known sample translated to partial sequencing at the pixel. In one implementation, a trainer 1724 varies a learning rate for the gradient descent over training epochs.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

What is claimed is:

1. A computer-implemented method of determining tag signals from measured intensities, the measured intensities collected by light sensors in a sensor array directed to a sample surface, the sample surface including pixel areas and holding a plurality of clusters during a sequence of sampling events, each light sensor directed to and measuring intensity from one of the pixel areas during each sampling period, the computer-implemented method including:
   determining an adjustment to the measured intensities from a pixel in the sampling periods for crosstalk from neighboring pixels by applying crosstalk estimations to measured intensities of the neighboring pixels in respective sampling periods;
   determining a further adjustment to the measured intensities from the pixel in the sampling periods for background intensity; and
   determining the tag signals originating from the pixel in the sampling periods, taking into account the adjustment and the further adjustment to the measured intensities, combined with modifying at least the measured intensities to take into account signal decay over progress of the sequence and for phasing and pre-phasing, including:
      modifying the measured intensities in the sampling periods by a progressive decay function that takes into account how late each sampling period occurs in the sequence; and
      applying a distribution function to at least current, prior and subsequent measured intensities, using signal presence ground truth for the pixel in the sampling periods, and separating intensity contributions due to phasing and pre-phasing from contribution of a current tag signal to the current measured intensity.

2. The computer-implemented method of claim 1, wherein the distribution function for phasing and pre-phasing takes into account a broadening distribution over progress of the sequence.

3. The computer-implemented method of claim 2, wherein the broadening distribution is determined by repeatedly convolving a phasing kernel with itself.

4. The computer-implemented method of claim 3, wherein the phasing kernel includes three terms for probabilities of sequence processing advancing as intended, failing to advance and skipping ahead by one position.

5. The computer-implemented method of claim 3, wherein the phasing kernel includes five terms for probabilities of sequence processing advancing as intended, failing to advance, skipping ahead by one position, skipping ahead by two positions, and skipping ahead by three positions.

6. The computer-implemented method of claim 1, wherein the decay function is an exponential decay.

7. The computer-implemented method of claim 1, wherein the adjustment for background intensity is performed for the pixel using pixel-by-pixel background coefficients.

8. The computer-implemented method of claim 7, wherein the adjustment for background intensity is a proportion between 0.95 and 0.995 of a minimum measured intensity for the pixel over the measured intensities in the sequence.

9. The computer-implemented method of claim 8, wherein the proportion is determined taking into account interaction between crosstalk from the neighboring pixels and the background adjustment for the pixel and the neighboring pixels.

10. The computer-implemented method of claim 1, wherein the adjustment for crosstalk is performed for the pixel using a pixel-by-pixel crosstalk coefficients.

11. The computer-implemented method of claim 1, further including determining coefficients for the crosstalk estimation and coefficients for the background intensity and coefficients for the decay function and coefficients for the distribution function by applying gradient descent to the signal presence ground truth for the pixel and the measured intensities for the sequence of the sampling events for the pixel.

12. The computer-implemented method of claim 11, wherein the sampling events are applied to a known sample and the signal presence ground truth is based on reliable sequencing of the known sample translated to partial sequencing at the pixel.

13. The computer-implemented method of claim 11, further including varying a learning rate for the gradient descent over training epochs.

14. A non-transitory computer readable storage medium impressed with computer program instructions to determine tag signals from measured intensities, the measured intensities collected by light sensors in a sensor array directed to a sample surface, the sample surface including pixel areas and holding a plurality of clusters during a sequence of sampling events, each light sensor directed to and measuring intensity from one of the pixel areas during each sampling period, the instructions, when executed on a processor, implement a method comprising:
  determining an adjustment to the measured intensities from a pixel in the sampling periods for crosstalk from neighboring pixels by applying crosstalk estimations to measured intensities of the neighboring pixels in respective sampling periods;
  determining a further adjustment to the measured intensities from the pixel in the sampling periods for background intensity; and
  determining the tag signals originating from the pixel in the sampling periods, taking into account the adjustment and the further adjustment to the measured intensities, combined with modifying at least the measured intensities to take into account signal decay over progress of the sequence and for phasing and pre-phasing, including:
    modifying the measured intensities in the sampling periods by a progressive decay function that takes into account how late each sampling period occurs in the sequence; and
    applying a distribution function to at least current, prior and subsequent measured intensities, using signal presence ground truth for the pixel in the sampling periods, and separating intensity contributions due to phasing and pre-phasing from contribution of a current tag signal to the current measured intensity.

15. The non-transitory computer readable storage medium of claim 14, wherein the distribution function for phasing and pre-phasing takes into account a broadening distribution over progress of the sequence.

16. The non-transitory computer readable storage medium of claim 15, wherein the broadening distribution is determined by repeatedly convolving a phasing kernel with itself.

17. The non-transitory computer readable storage medium of claim 16, wherein the phasing kernel includes three terms for probabilities of sequence processing advancing as intended, failing to advance and skipping ahead by one position.

18. The non-transitory computer readable storage medium of claim 16, wherein the phasing kernel includes five terms for probabilities of sequence processing advancing as intended, failing to advance, skipping ahead by one position, skipping ahead by two positions, and skipping ahead by three positions.

19. The non-transitory computer readable storage medium of claim 14, wherein the decay function is an exponential decay.

20. A system including one or more processors coupled to memory, the memory loaded with computer instructions to determine tag signals from measured intensities, the measured intensities collected by light sensors in a sensor array directed to a sample surface, the sample surface including pixel areas and holding a plurality of clusters during a sequence of sampling events, each light sensor directed to and measuring intensity from one of the pixel areas during each sampling period, the instructions, when executed on the processors, implement actions comprising:
  determining an adjustment to the measured intensities from a pixel in the sampling periods for crosstalk from neighboring pixels by applying crosstalk estimations to measured intensities of the neighboring pixels in respective sampling periods;
  determining a further adjustment to the measured intensities from the pixel in the sampling periods for background intensity; and
  determining the tag signals originating from the pixel in the sampling periods, taking into account the adjustment and the further adjustment to the measured intensities, combined with modifying at least the measured intensities to take into account signal decay over progress of the sequence and for phasing and pre-phasing, including:
    modifying the measured intensities in the sampling periods by a progressive decay function that takes into account how late each sampling period occurs in the sequence; and
    applying a distribution function to at least current, prior and subsequent measured intensities, using signal presence ground truth for the pixel in the sampling periods, and separating intensity contributions due to phasing and pre-phasing from contribution of a current tag signal to the current measured intensity.

* * * * *